US012599563B1

(12) United States Patent
Churchill et al.

(10) Patent No.: US 12,599,563 B1
(45) Date of Patent: *Apr. 14, 2026

(54) PHARMACEUTICAL FORMULATIONS COMPRISING NALTREXONE AND/OR BUPROPION

(71) Applicant: Nalpropion Pharmaceuticals LLC, Brentwood, TN (US)

(72) Inventors: Rob Churchill, Nolensville, TN (US); Aaron Chesnut, Nolensville, TN (US)

(73) Assignee: Nalpropion Pharmaceuticals LLC, Brentwood, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/211,696

(22) Filed: May 19, 2025

Related U.S. Application Data

(62) Division of application No. 18/917,080, filed on Oct. 16, 2024, now Pat. No. 12,303,604.

(51) Int. Cl.
| | |
|---|---|
| *A61K 9/48* | (2006.01) |
| *A61K 9/00* | (2006.01) |
| *A61K 9/20* | (2006.01) |
| *A61K 31/137* | (2006.01) |
| *A61K 31/485* | (2006.01) |

(52) U.S. Cl.
CPC .......... *A61K 9/2081* (2013.01); *A61K 9/0053* (2013.01); *A61K 9/2013* (2013.01); *A61K 9/2054* (2013.01); *A61K 31/137* (2013.01); *A61K 31/485* (2013.01)

(58) Field of Classification Search
CPC .......... A61K 9/28; A61K 9/2886; A61K 9/48; A61K 9/4808
See application file for complete search history.

(56) References Cited

U.S. PATENT DOCUMENTS

| | | | |
|---|---|---|---|
| 5,512,593 | A | 4/1996 | Dante |
| 5,817,665 | A | 10/1998 | Dante |
| 6,004,970 | A | 12/1999 | O'malley et al. |
| 6,034,091 | A | 3/2000 | Dante |
| 6,096,341 | A | 8/2000 | Seth |
| 6,228,397 | B1 | 5/2001 | Shen et al. |
| 6,228,398 | B1 | 5/2001 | Devane et al. |
| 6,299,901 | B1 | 10/2001 | Disanto et al. |
| 6,316,031 | B1 | 11/2001 | Oshlack et al. |
| 6,319,954 | B1 | 11/2001 | Disanto |
| 6,323,236 | B2 | 11/2001 | Mcelroy |
| 6,365,184 | B1 | 4/2002 | Depui et al. |
| 6,419,960 | B1 | 7/2002 | Krishnamurthy et al. |
| 6,511,477 | B2 | 1/2003 | Altman et al. |
| 6,541,478 | B1 | 4/2003 | O'malley et al. |
| 6,576,260 | B2 | 6/2003 | Bartholomaeus et al. |
| 6,622,036 | B1 | 9/2003 | Suffin |
| 6,627,223 | B2 | 9/2003 | Percel et al. |
| 6,635,284 | B2 | 10/2003 | Mehta et al. |

| | | | |
|---|---|---|---|
| 6,696,088 | B2 | 2/2004 | Oshlack et al. |
| 6,699,508 | B1 | 3/2004 | Sugi et al. |
| 6,770,620 | B2 | 8/2004 | Henriksen |
| 6,827,947 | B2 | 12/2004 | Lofroth et al. |
| 6,905,708 | B2 | 6/2005 | Li et al. |
| 6,911,217 | B1 | 6/2005 | Gren et al. |
| 6,969,525 | B2 | 11/2005 | Chow |
| 6,991,807 | B2 | 1/2006 | Rudnic et al. |
| 7,022,342 | B2 | 4/2006 | Chen et al. |
| 7,083,808 | B2 | 8/2006 | Goldenheim et al. |
| 7,090,830 | B2 | 8/2006 | Hale et al. |
| 7,186,683 | B2 | 3/2007 | Henriksen et al. |
| 7,220,434 | B2 | 5/2007 | Desai et al. |
| 7,303,761 | B2 | 12/2007 | Franz |
| 7,314,640 | B2 | 1/2008 | Sriwongjanya et al. |
| 7,374,779 | B2 | 5/2008 | Chen et al. |
| 7,375,111 | B2 | 5/2008 | Weber et al. |
| 7,384,653 | B2 | 6/2008 | Wright, IV et al. |
| 7,416,738 | B2 | 8/2008 | Sowden et al. |
| 7,462,626 | B2 | 12/2008 | Weber et al. |
| 7,489,964 | B2 | 2/2009 | Suffin et al. |
| 7,524,515 | B2 | 4/2009 | Roberts |
| 7,658,918 | B1 | 2/2010 | Ortenzi et al. |
| 7,662,987 | B2 | 2/2010 | Bhat et al. |
| 7,670,627 | B2 | 3/2010 | Shefer et al. |
| 7,682,634 | B2 | 3/2010 | Matthews |
| 7,744,924 | B2 | 6/2010 | Heinicke |
| 7,790,215 | B2 | 9/2010 | Sackler et al. |
| 7,825,087 | B2 | 11/2010 | Jenkins et al. |
| 7,858,118 | B2 | 12/2010 | Deboeck et al. |
| 7,858,609 | B2 | 12/2010 | Shaw et al. |
| 7,879,362 | B2 | 2/2011 | Castan et al. |

(Continued)

FOREIGN PATENT DOCUMENTS

| | | | |
|---|---|---|---|
| WO | 2005016318 A1 | 2/2005 | |
| WO | WO-2012075459 A1 * | 6/2012 | .............. A61P 43/00 |

(Continued)

OTHER PUBLICATIONS

"Contrave U.S. Label, Revised May 2024, 44 pages".
Apostolidi et al., "Dissolution Assay of Bupropion/Naltrexone Hydrochloride Salts of Bilayer Composition Tablets Following the Development and Validation of a Novel HPLC Method", Materials 2022, 15, 8451, 13 pages.
Siamidi, et al., "Probing the Release of Bupropion and Naltrexone Hydrochloride Salta from Biopolymeric Matrices of Diverse Chemical Structures", Polymers 2021, 13, 1456, 18 pages.
Abdul, et al., "A flexible technology for modified-release drus: Multiple-unit pellet system (MUPS)", Journal of Controlled Released, vol. 147, (2010) 2-16.

(Continued)

*Primary Examiner* — Micah Paul Young
(74) *Attorney, Agent, or Firm* — Servilla Whitney LLC

(57) ABSTRACT

Described are pharmaceutical formulations comprising naltrexone and/or bupropion. Such pharmaceutical formulations can comprise extended-release, multilayer beads. Also described are methods of administering such formulations, such as for the treatment of overweight or obesity.

30 Claims, 10 Drawing Sheets

(56)                   References Cited

U.S. PATENT DOCUMENTS

| | | | |
|---|---|---|---|
| 7,910,128 B2 | 3/2011 | Chang et al. |
| 7,914,818 B2 | 3/2011 | Breder et al. |
| 7,915,285 B2 | 3/2011 | Johnson et al. |
| 7,919,499 B2 | 4/2011 | Ehrich |
| 7,939,102 B2 | 5/2011 | Nadkarni et al. |
| 7,964,216 B2 | 6/2011 | Shanghvi et al. |
| 7,976,871 B2 | 7/2011 | Vaya et al. |
| 7,985,422 B2 | 7/2011 | Vaya et al. |
| 8,044,021 B2 | 10/2011 | Hossainy et al. |
| 8,062,666 B2 | 11/2011 | Sela |
| 8,062,672 B2 | 11/2011 | Burnside et al. |
| 8,088,786 B2 | 1/2012 | Mckinney et al. |
| 8,106,021 B2 | 1/2012 | Chen et al. |
| 8,110,226 B2 | 2/2012 | Li |
| 8,124,126 B2 | 2/2012 | Bosse et al. |
| 8,187,617 B2 | 5/2012 | Howard et al. |
| 8,221,787 B2 | 7/2012 | Jung et al. |
| 8,252,330 B2 | 8/2012 | Kamath et al. |
| 8,263,125 B2 | 9/2012 | Vaya et al. |
| 8,268,352 B2 | 9/2012 | Vaya et al. |
| 8,298,579 B2 | 10/2012 | Abreu |
| 8,298,580 B2 | 10/2012 | Liang et al. |
| 8,318,778 B2 | 11/2012 | Murray et al. |
| 8,318,788 B2 | 11/2012 | Mckinney et al. |
| 8,318,813 B2 | 11/2012 | Sanfilippo |
| 8,367,111 B2 | 2/2013 | Venkatesh |
| 8,377,474 B2 | 2/2013 | Hsu et al. |
| 8,394,415 B2 | 3/2013 | Lee et al. |
| 8,426,439 B2 | 4/2013 | Ciccocioppo |
| 8,431,532 B2 | 4/2013 | Brennan et al. |
| 8,465,768 B2 | 6/2013 | Park et al. |
| 8,512,748 B2 | 8/2013 | Pearnchob et al. |
| 8,535,713 B2 | 9/2013 | Coulter |
| 8,541,026 B2 | 9/2013 | Qiu et al. |
| 8,562,951 B2 | 10/2013 | Suffin et al. |
| 8,586,103 B2 | 11/2013 | Li et al. |
| 8,603,520 B2 | 12/2013 | Odidi et al. |
| 8,617,602 B2 | 12/2013 | Howard et al. |
| 8,653,271 B2 | 2/2014 | Stinchcomb et al. |
| 8,679,546 B2 | 3/2014 | Cavassini et al. |
| 8,709,491 B2 | 4/2014 | Tengler et al. |
| 8,722,085 B2 | 5/2014 | Mckinney et al. |
| 8,729,017 B2 | 5/2014 | Dimarchi et al. |
| 8,741,345 B2 | 6/2014 | Cifter et al. |
| 8,741,350 B2 | 6/2014 | Folger et al. |
| 8,796,338 B2 | 8/2014 | Baron et al. |
| 8,815,285 B2 | 8/2014 | Mandaogade et al. |
| 8,815,889 B2 | 8/2014 | Cowley et al. |
| 8,825,164 B2 | 9/2014 | Tweden et al. |
| 8,846,053 B2 | 9/2014 | Geho et al. |
| 8,853,412 B2 | 10/2014 | Schwink et al. |
| 8,865,213 B2 | 10/2014 | Sheth et al. |
| 8,883,208 B2 | 11/2014 | Mcgonigle et al. |
| 8,895,063 B2 | 11/2014 | Guimberteau et al. |
| 8,911,781 B2 | 12/2014 | Antarkar et al. |
| 8,916,195 B2 | 12/2014 | Mckinney et al. |
| 8,927,553 B2 | 1/2015 | Dhanoa |
| 8,969,371 B1 | 3/2015 | Klassen et al. |
| 8,992,973 B2 | 3/2015 | Rekhi et al. |
| 8,992,974 B2 | 3/2015 | Mccarty |
| 9,005,658 B2 | 4/2015 | Schlutermann et al. |
| 9,011,907 B2 | 4/2015 | Ravishankar et al. |
| 9,016,221 B2 | 4/2015 | Brennan et al. |
| 9,040,086 B2 | 5/2015 | Percel et al. |
| 9,050,292 B2 | 6/2015 | Baron et al. |
| 9,078,830 B2 | 7/2015 | Jain et al. |
| 9,095,513 B2 | 8/2015 | Tanji et al. |
| 9,095,519 B2 | 8/2015 | Blundell et al. |
| 9,107,804 B2 | 8/2015 | Rubino et al. |
| 9,107,837 B2 | 8/2015 | Mckinney et al. |
| 9,119,809 B2 | 9/2015 | Lickrish et al. |
| 9,119,850 B2 | 9/2015 | Klassen et al. |
| 9,125,868 B2 | 9/2015 | Mckinney et al. |
| 9,132,096 B1 | 9/2015 | Rekhi et al. |
| 9,145,453 B2 | 9/2015 | Geho et al. |
| 9,149,436 B2 | 10/2015 | Oshlack et al. |
| 9,149,439 B2 | 10/2015 | Patel et al. |
| 9,149,460 B2 | 10/2015 | Humar et al. |
| 9,156,902 B2 | 10/2015 | Dimarchi et al. |
| 9,161,919 B2 | 10/2015 | Venkatesh |
| 9,180,101 B2 | 11/2015 | Oh et al. |
| 9,186,392 B2 | 11/2015 | Klein et al. |
| 9,186,502 B2 | 11/2015 | Kim et al. |
| 9,211,263 B2 | 12/2015 | Baron et al. |
| 9,220,681 B2 | 12/2015 | Coulter et al. |
| 9,220,715 B2 | 12/2015 | Demopulos et al. |
| 9,241,910 B2 | 1/2016 | Kurasawa et al. |
| 9,248,123 B2 | 2/2016 | Dunayevich et al. |
| 9,259,394 B2 | 2/2016 | Bagchi et al. |
| 9,265,277 B2 | 2/2016 | Gellenbeck et al. |
| 9,265,732 B2 | 2/2016 | Plachetka et al. |
| 9,265,760 B2 | 2/2016 | Hartman et al. |
| 9,278,094 B2 | 3/2016 | Bear et al. |
| 9,364,440 B2 | 6/2016 | Gonzalez et al. |
| 9,365,632 B2 | 6/2016 | Haack et al. |
| 9,381,162 B2 | 7/2016 | Baumler et al. |
| 9,415,013 B2 | 8/2016 | Paborji et al. |
| 9,433,583 B2 | 9/2016 | Farrell |
| 9,434,778 B2 | 9/2016 | Morin et al. |
| 9,440,949 B2 | 9/2016 | Cabral et al. |
| 9,447,108 B2 | 9/2016 | Fulop et al. |
| 9,457,005 B2 | 10/2016 | Cowley et al. |
| 9,463,170 B2 | 10/2016 | Baron et al. |
| 9,480,663 B2 | 11/2016 | Baron et al. |
| 9,481,642 B2 | 11/2016 | Baron et al. |
| 9,504,655 B2 | 11/2016 | Vats et al. |
| 9,561,179 B2 | 2/2017 | Castan et al. |
| 9,561,188 B2 | 2/2017 | Odidi et al. |
| 9,572,781 B2 | 2/2017 | Venkatesh et al. |
| 9,579,286 B2 | 2/2017 | Oshlack et al. |
| 9,598,401 B2 | 3/2017 | Zhang et al. |
| 9,610,285 B2 | 4/2017 | Avena et al. |
| 9,633,575 B2 | 4/2017 | Klassen et al. |
| 9,642,801 B2 | 5/2017 | Sesha |
| 9,675,670 B2 | 6/2017 | Clokie et al. |
| 9,694,053 B2 | 7/2017 | Haack et al. |
| 9,714,232 B2 | 7/2017 | Zhang et al. |
| 9,744,137 B2 | 8/2017 | Nangia et al. |
| 9,745,360 B2 | 8/2017 | Haack et al. |
| 9,750,788 B2 | 9/2017 | Kadereit et al. |
| 9,751,926 B2 | 9/2017 | Kadereit et al. |
| 9,758,561 B2 | 9/2017 | Bossart et al. |
| 9,765,089 B2 | 9/2017 | Greenwood et al. |
| 9,770,422 B2 | 9/2017 | Baron et al. |
| 9,770,514 B2 | 9/2017 | Ghebre-sellassie et al. |
| 9,771,406 B2 | 9/2017 | Bossart et al. |
| 9,775,904 B2 | 10/2017 | Bossart et al. |
| 9,782,416 B2 | 10/2017 | Cowen |
| 9,789,165 B2 | 10/2017 | Kadereit et al. |
| 9,801,875 B2 | 10/2017 | Klassen et al. |
| 9,821,024 B2 | 11/2017 | Aversa et al. |
| 9,827,204 B2 | 11/2017 | Haswani et al. |
| 9,839,626 B1 | 12/2017 | Agarwal et al. |
| 9,895,318 B2 | 2/2018 | Joshi et al. |
| 9,896,495 B2 | 2/2018 | Riber et al. |
| 9,956,194 B2 | 5/2018 | Ohlstein et al. |
| 9,962,344 B2 | 5/2018 | Baron et al. |
| 9,974,752 B2 | 5/2018 | Vargas Rincon et al. |
| 9,982,029 B2 | 5/2018 | Bossart et al. |
| 10,011,637 B2 | 7/2018 | Shailubhai et al. |
| 10,028,923 B2 | 7/2018 | Baron et al. |
| 10,064,828 B1 | 9/2018 | Odidi et al. |
| 10,064,850 B2 | 9/2018 | Ciccocioppo |
| 10,154,856 B2 | 12/2018 | Sillender |
| 10,154,972 B2 | 12/2018 | Baron et al. |
| 10,166,196 B2 | 1/2019 | Yan et al. |
| 10,166,228 B2 | 1/2019 | Brittain et al. |
| 10,201,511 B2 | 2/2019 | Baron et al. |
| 10,213,586 B2 | 2/2019 | Netzel et al. |
| 10,231,962 B2 | 3/2019 | Klassen et al. |
| 10,231,964 B2 | 3/2019 | Klassen et al. |
| 10,245,233 B2 | 4/2019 | Van Ommen |
| 10,253,102 B2 | 4/2019 | Gromada et al. |
| 10,258,577 B2 | 4/2019 | Chen et al. |

(56) References Cited

U.S. PATENT DOCUMENTS

| | | | |
|---|---|---|---|
| 10,307,376 B2 | 6/2019 | Mckinney et al. |
| 10,322,121 B2 | 6/2019 | Dunayevich et al. |
| 10,403,170 B2 | 9/2019 | Klassen et al. |
| 10,406,234 B2 | 9/2019 | Vaka et al. |
| 10,434,138 B2 | 10/2019 | Coulter et al. |
| 10,457,714 B2 | 10/2019 | Riber et al. |
| 10,500,180 B2 | 12/2019 | Reiner et al. |
| 10,519,211 B2 | 12/2019 | Bossart et al. |
| 10,549,052 B2 | 2/2020 | Shahaf et al. |
| 10,561,602 B2 | 2/2020 | Odidi |
| 10,561,650 B2 | 2/2020 | Reid |
| 10,603,291 B2 | 3/2020 | Baron et al. |
| 10,610,500 B2 | 4/2020 | Baron et al. |
| 10,618,968 B2 | 4/2020 | Gromada et al. |
| 10,624,858 B2 | 4/2020 | Odidi |
| 10,668,031 B2 | 6/2020 | Baron et al. |
| 10,716,761 B2 | 7/2020 | First et al. |
| 10,716,784 B2 | 7/2020 | James et al. |
| 10,730,923 B2 | 8/2020 | Dimarchi et al. |
| 10,828,294 B2 | 11/2020 | Klassen et al. |
| 10,835,527 B2 | 11/2020 | Klassen et al. |
| 10,881,665 B2 | 1/2021 | Javitt |
| 10,940,159 B2 | 3/2021 | Green et al. |
| 11,026,908 B2 | 6/2021 | Sela et al. |
| 11,033,508 B2 | 6/2021 | Lai et al. |
| 11,033,509 B2 | 6/2021 | Karki et al. |
| 11,033,543 B2 | 6/2021 | Dunayevich et al. |
| 11,052,047 B2 | 7/2021 | Wittorff |
| 11,058,641 B2 | 7/2021 | Wittorff |
| 11,139,056 B2 | 10/2021 | Klassen et al. |
| 11,166,947 B2 | 11/2021 | Tengler et al. |
| 11,260,030 B2 | 3/2022 | Wittorff |
| 11,278,544 B2 | 3/2022 | Weber et al. |
| 11,285,153 B2 | 3/2022 | Jin et al. |
| 11,285,306 B2 | 3/2022 | Johnston et al. |
| 11,291,642 B2 | 4/2022 | Boulas et al. |
| 11,311,490 B2 | 4/2022 | Schlutermann et al. |
| 11,324,741 B2 | 5/2022 | Tollefson |
| 11,337,943 B2 | 5/2022 | Lyu et al. |
| 11,344,506 B2 | 5/2022 | Bernardo et al. |
| 11,344,556 B2 | 5/2022 | Bentz |
| 11,383,048 B2 | 7/2022 | Shahaf et al. |
| 11,446,627 B2 | 9/2022 | Cardoso et al. |
| 11,504,342 B2 | 11/2022 | Vasisht et al. |
| 11,542,315 B2 | 1/2023 | Bowrey et al. |
| 11,564,885 B2 | 1/2023 | Mateen et al. |
| 11,608,381 B2 | 3/2023 | Gromada et al. |
| 11,740,247 B2 | 8/2023 | Acosta et al. |
| 11,819,482 B2 | 11/2023 | Hansen et al. |
| 11,872,307 B2 | 1/2024 | Zhao et al. |
| 11,938,164 B2 | 3/2024 | Denis et al. |
| 11,939,635 B2 | 3/2024 | Lotta et al. |
| 11,957,704 B2 | 4/2024 | Lotta et al. |
| 11,998,542 B2 | 6/2024 | Klassen et al. |
| 12,042,614 B2 | 7/2024 | Johnston et al. |
| 12,048,769 B2 | 7/2024 | Mckinney et al. |
| 12,109,312 B2 | 10/2024 | Wittorff |
| 12,121,564 B2 | 10/2024 | Andreakos et al. |
| 12,128,142 B2 | 10/2024 | Haddleton et al. |
| 2001/0018457 A1 | 8/2001 | Disanto et al. |
| 2001/0053798 A1 | 12/2001 | Disanto |
| 2002/0037836 A1 | 3/2002 | Henriksen |
| 2002/0119196 A1 | 8/2002 | Parikh et al. |
| 2003/0013692 A1 | 1/2003 | Gullans et al. |
| 2003/0050620 A1 | 3/2003 | Odidi et al. |
| 2003/0087896 A1 | 5/2003 | Glover |
| 2003/0144271 A1 | 7/2003 | Shulman |
| 2004/0052862 A1 | 3/2004 | Henriksen et al. |
| 2004/0059241 A1 | 3/2004 | Sutfin |
| 2004/0102440 A1 | 5/2004 | Wong |
| 2004/0204472 A1 | 10/2004 | Briggs et al. |
| 2004/0228915 A1 | 11/2004 | Noack et al. |
| 2004/0242974 A1 | 12/2004 | Glover |
| 2004/0254182 A1 | 12/2004 | Mulvihill et al. |
| 2005/0009870 A1 | 1/2005 | Sher et al. |
| 2005/0014786 A1 | 1/2005 | Sun et al. |
| 2005/0019411 A1 | 1/2005 | Colombo et al. |
| 2005/0054659 A1 | 3/2005 | Ellsworth et al. |
| 2005/0074493 A1 | 4/2005 | Mehta et al. |
| 2005/0080087 A1 | 4/2005 | Pendri et al. |
| 2005/0089571 A1 | 4/2005 | Beckert et al. |
| 2005/0143381 A1 | 6/2005 | Yu et al. |
| 2005/0171110 A1 | 8/2005 | Yu et al. |
| 2006/0018933 A1 | 1/2006 | Vaya et al. |
| 2006/0099258 A1 | 5/2006 | Heinicke |
| 2006/0099259 A1 | 5/2006 | Heinicke |
| 2006/0115526 A1 | 6/2006 | Doshi et al. |
| 2006/0120962 A1 | 6/2006 | Rabinowitz et al. |
| 2006/0121114 A1 | 6/2006 | Antarkar et al. |
| 2006/0127484 A1 | 6/2006 | Speirs et al. |
| 2006/0198815 A1 | 9/2006 | Barker et al. |
| 2006/0204575 A1 | 9/2006 | Feng et al. |
| 2006/0240105 A1 | 10/2006 | Devane et al. |
| 2006/0251722 A1 | 11/2006 | Bandak et al. |
| 2006/0269596 A1 | 11/2006 | Liversidge et al. |
| 2006/0269605 A1 | 11/2006 | Lizio et al. |
| 2006/0280795 A1 | 12/2006 | Penhasi et al. |
| 2007/0003621 A1 | 1/2007 | Nangia et al. |
| 2007/0009589 A1 | 1/2007 | Raghupathi et al. |
| 2007/0020339 A1 | 1/2007 | Bear |
| 2007/0042045 A1 | 2/2007 | Lizio et al. |
| 2007/0043096 A1 | 2/2007 | Tidmarsh et al. |
| 2007/0059346 A1 | 3/2007 | Maibach |
| 2007/0065512 A1 | 3/2007 | Dedhiya et al. |
| 2007/0071806 A1 | 3/2007 | Mccarty |
| 2007/0082051 A1 | 4/2007 | Ravelli et al. |
| 2007/0098778 A1 | 5/2007 | Borsadia |
| 2007/0098791 A1 | 5/2007 | Rekhi et al. |
| 2007/0116729 A1 | 5/2007 | Palepu |
| 2007/0117827 A1 | 5/2007 | Tollefson et al. |
| 2007/0128276 A1 | 6/2007 | Jain et al. |
| 2007/0129283 A1 | 6/2007 | Mckinney et al. |
| 2007/0148237 A1 | 6/2007 | Mckinney et al. |
| 2007/0155664 A1 | 7/2007 | Ranklove et al. |
| 2007/0179168 A1 | 8/2007 | Cowley et al. |
| 2007/0190141 A1 | 8/2007 | Dely |
| 2007/0190145 A1 | 8/2007 | Venkatesh et al. |
| 2007/0196491 A1 | 8/2007 | Venkatesh |
| 2007/0202162 A1 | 8/2007 | Sankarnarayanan et al. |
| 2007/0202170 A1 | 8/2007 | Desai et al. |
| 2007/0202172 A1 | 8/2007 | Gold et al. |
| 2007/0243245 A1 | 10/2007 | Heinicke |
| 2007/0243250 A1 | 10/2007 | Heinicke |
| 2007/0248670 A1 | 10/2007 | Van Den Heuvel |
| 2007/0264346 A1 | 11/2007 | Guimberteau et al. |
| 2007/0269505 A1 | 11/2007 | Flath et al. |
| 2007/0270450 A1 | 11/2007 | Weber et al. |
| 2007/0275066 A1 | 11/2007 | Cho et al. |
| 2007/0275970 A1 | 11/2007 | Weber et al. |
| 2007/0292523 A1 | 12/2007 | Moodley et al. |
| 2007/0298098 A1 | 12/2007 | Jenkins et al. |
| 2008/0009477 A1 | 1/2008 | Hutchison |
| 2008/0050449 A1 | 2/2008 | Arieli et al. |
| 2008/0057122 A1 | 3/2008 | Toney-parker et al. |
| 2008/0066739 A1 | 3/2008 | Lemahieu et al. |
| 2008/0066741 A1 | 3/2008 | Lemahieu et al. |
| 2008/0069870 A1 | 3/2008 | Jenkins et al. |
| 2008/0078382 A1 | 4/2008 | Lemahieu et al. |
| 2008/0102121 A1 | 5/2008 | Devane et al. |
| 2008/0110792 A1 | 5/2008 | Mckinney et al. |
| 2008/0113025 A1 | 5/2008 | Devane et al. |
| 2008/0113026 A1 | 5/2008 | Mckinney et al. |
| 2008/0118554 A1 | 5/2008 | Ari-pardo et al. |
| 2008/0131492 A1 | 6/2008 | Nangia et al. |
| 2008/0139624 A1 | 6/2008 | Re |
| 2008/0152719 A1 | 6/2008 | Petereit et al. |
| 2008/0171692 A1 | 7/2008 | Hagmann |
| 2008/0187579 A1 | 8/2008 | Bhat et al. |
| 2008/0214592 A1 | 9/2008 | Cowley et al. |
| 2008/0220080 A1 | 9/2008 | Petereit et al. |
| 2008/0226719 A1 | 9/2008 | Roses et al. |
| 2008/0226722 A1 | 9/2008 | Van Tomme et al. |
| 2008/0233156 A1 | 9/2008 | Matthews et al. |
| 2008/0255073 A1 | 10/2008 | Gallop et al. |

(56) References Cited

U.S. PATENT DOCUMENTS

| | | |
|---|---|---|
| 2008/0268043 A1 | 10/2008 | Jenkins et al. |
| 2008/0293777 A1 | 11/2008 | Erianson et al. |
| 2008/0317845 A1 | 12/2008 | Persicaner et al. |
| 2009/0004281 A1 | 1/2009 | Nghiem et al. |
| 2009/0017102 A1 | 1/2009 | Stinchcomb |
| 2009/0017111 A1 | 1/2009 | Van Den Heuvel |
| 2009/0023778 A1 | 1/2009 | Kimura et al. |
| 2009/0028935 A1 | 1/2009 | Arnold et al. |
| 2009/0036426 A1 | 2/2009 | Hauske |
| 2009/0068260 A1 | 3/2009 | Gold et al. |
| 2009/0087487 A1 | 4/2009 | Fox et al. |
| 2009/0131466 A1 | 5/2009 | Liang et al. |
| 2009/0143361 A1 | 6/2009 | Malamas et al. |
| 2009/0143367 A1 | 6/2009 | Malamas et al. |
| 2009/0157662 A1 | 6/2009 | Suffin et al. |
| 2009/0196890 A1 | 8/2009 | Liang et al. |
| 2009/0208572 A1 | 8/2009 | Bhalachandra et al. |
| 2009/0214643 A1 | 8/2009 | Franklin et al. |
| 2009/0214665 A1 | 8/2009 | Lai et al. |
| 2009/0220611 A1 | 9/2009 | Dargelas et al. |
| 2009/0239841 A1 | 9/2009 | Hutchison et al. |
| 2009/0252807 A1 | 10/2009 | Jenkins et al. |
| 2009/0258066 A1 | 10/2009 | Venkatesh et al. |
| 2009/0264489 A1 | 10/2009 | Hildebrand et al. |
| 2009/0291137 A1 | 11/2009 | Guimberteau et al. |
| 2010/0092557 A1 | 4/2010 | Vergnault et al. |
| 2010/0113496 A1 | 5/2010 | Gant |
| 2010/0183598 A1 | 7/2010 | Schultz et al. |
| 2010/0190793 A1 | 7/2010 | Weber et al. |
| 2010/0215737 A1 | 8/2010 | Coulter |
| 2010/0255091 A1 | 10/2010 | Ranzani et al. |
| 2010/0317572 A1 | 12/2010 | Mikkelsen |
| 2011/0028505 A1 | 2/2011 | Mckinney et al. |
| 2011/0060037 A1 | 3/2011 | Woldbye et al. |
| 2011/0064803 A1 | 3/2011 | Devane et al. |
| 2011/0091566 A1 | 4/2011 | Mulye |
| 2011/0129530 A1 | 6/2011 | Venkatesh et al. |
| 2011/0144145 A1 | 6/2011 | Tollefson |
| 2011/0177165 A1 | 7/2011 | Gerber et al. |
| 2011/0229564 A1 | 9/2011 | Desai et al. |
| 2011/0230461 A1 | 9/2011 | Bhattacharya et al. |
| 2011/0311626 A1 | 12/2011 | Venkatesh et al. |
| 2012/0010232 A1 | 1/2012 | Weber et al. |
| 2012/0035105 A1 | 2/2012 | Geho et al. |
| 2012/0058194 A1 | 3/2012 | Vaya et al. |
| 2012/0065179 A1 | 3/2012 | Andersson |
| 2012/0093939 A1 | 4/2012 | Payne et al. |
| 2012/0109712 A1 | 5/2012 | Lloyd et al. |
| 2012/0115849 A1 | 5/2012 | Demopulos et al. |
| 2012/0121724 A1 | 5/2012 | Maibach |
| 2012/0135960 A2 | 5/2012 | Mouthon et al. |
| 2012/0141554 A1 | 6/2012 | Dill |
| 2012/0207825 A1 | 8/2012 | Roy et al. |
| 2013/0052264 A1 | 2/2013 | Chung et al. |
| 2013/0089577 A1 | 4/2013 | St. Laurent et al. |
| 2013/0116215 A1 | 5/2013 | Coma et al. |
| 2013/0177602 A1 | 7/2013 | Mckinney et al. |
| 2013/0202705 A1 | 8/2013 | Hamed |
| 2013/0245056 A1 | 9/2013 | Flanagan et al. |
| 2013/0252908 A1 | 9/2013 | Mayoux et al. |
| 2013/0252995 A1 | 9/2013 | Dunayevich et al. |
| 2013/0296347 A1 | 11/2013 | Ciccocioppo |
| 2014/0030343 A1 | 1/2014 | Lamson et al. |
| 2014/0050797 A1* | 2/2014 | Venkatesh .................. A61P 9/10 424/494 |
| 2014/0073664 A1 | 3/2014 | Wang et al. |
| 2014/0080756 A1 | 3/2014 | Bhattacharya et al. |
| 2014/0080857 A1 | 3/2014 | Mckinney et al. |
| 2014/0112995 A1 | 4/2014 | Bhavarisetti et al. |
| 2014/0161879 A1 | 6/2014 | Hartman et al. |
| 2014/0178468 A1 | 6/2014 | Shear et al. |
| 2014/0193498 A1 | 7/2014 | Baron et al. |
| 2014/0206608 A1 | 7/2014 | Haack et al. |
| 2014/0206609 A1 | 7/2014 | Haack et al. |
| 2014/0213513 A1 | 7/2014 | Haack et al. |
| 2014/0271892 A1 | 9/2014 | Lee et al. |
| 2014/0271923 A1 | 9/2014 | Reid |
| 2014/0309252 A1 | 10/2014 | Mckinney et al. |
| 2014/0357600 A1 | 12/2014 | St. Laurent et al. |
| 2014/0363516 A1 | 12/2014 | Rother et al. |
| 2015/0086623 A1 | 3/2015 | Chung et al. |
| 2015/0111817 A1 | 4/2015 | Riber et al. |
| 2015/0119417 A1 | 4/2015 | Tollefson |
| 2015/0141452 A1 | 5/2015 | Weber et al. |
| 2015/0164806 A1 | 6/2015 | Mckinney et al. |
| 2015/0166625 A1 | 6/2015 | Haack et al. |
| 2015/0174116 A1 | 6/2015 | Mccarty |
| 2015/0272915 A1 | 10/2015 | Mouthon et al. |
| 2015/0297610 A1 | 10/2015 | Sanchez et al. |
| 2015/0306170 A1 | 10/2015 | Ahuja et al. |
| 2015/0342946 A1 | 12/2015 | Bear et al. |
| 2015/0366825 A1 | 12/2015 | Joshi et al. |
| 2015/0368311 A1 | 12/2015 | Haack et al. |
| 2016/0022591 A1 | 1/2016 | Kirsch et al. |
| 2016/0058881 A1 | 3/2016 | Dimarchi et al. |
| 2016/0081943 A1 | 3/2016 | Anness et al. |
| 2016/0158221 A1 | 6/2016 | Mckinney et al. |
| 2016/0158225 A1 | 6/2016 | Mckinney et al. |
| 2016/0193152 A1 | 7/2016 | Mckinney et al. |
| 2016/0220561 A1 | 8/2016 | Garegnani et al. |
| 2016/0220562 A1 | 8/2016 | Garegnani et al. |
| 2016/0256472 A1 | 9/2016 | O'Neil |
| 2016/0263102 A1 | 9/2016 | Garegnani et al. |
| 2016/0271143 A1 | 9/2016 | Ryazanov et al. |
| 2016/0279056 A1 | 9/2016 | Zhao et al. |
| 2016/0310484 A1 | 10/2016 | Bear et al. |
| 2016/0338965 A1 | 11/2016 | Mckinney et al. |
| 2016/0361278 A1 | 12/2016 | Kang et al. |
| 2017/0007598 A1 | 1/2017 | Weber et al. |
| 2017/0014404 A1 | 1/2017 | Mckinney et al. |
| 2017/0020990 A1 | 1/2017 | Cowley et al. |
| 2017/0049705 A1 | 2/2017 | Mateescu et al. |
| 2017/0101477 A1 | 4/2017 | Gromada et al. |
| 2017/0128424 A1 | 5/2017 | Rothstein |
| 2017/0143712 A1 | 5/2017 | Lannutti et al. |
| 2017/0173037 A1 | 6/2017 | Bosse et al. |
| 2017/0196985 A1 | 7/2017 | Dong et al. |
| 2017/0296476 A1 | 10/2017 | Wening et al. |
| 2017/0312269 A1 | 11/2017 | Mckinney et al. |
| 2017/0319521 A1 | 11/2017 | Dill |
| 2018/0015042 A1 | 1/2018 | Sehgal et al. |
| 2018/0031541 A1 | 2/2018 | Miller et al. |
| 2018/0049979 A1 | 2/2018 | Zhao et al. |
| 2018/0104191 A1 | 4/2018 | Zhu et al. |
| 2018/0161281 A1 | 6/2018 | Kanniyappan et al. |
| 2018/0179188 A1 | 6/2018 | Zhang et al. |
| 2018/0215737 A1 | 8/2018 | Zhang et al. |
| 2018/0280405 A1 | 10/2018 | Cowen |
| 2018/0318289 A1 | 11/2018 | Bear et al. |
| 2018/0355010 A1 | 12/2018 | Riber et al. |
| 2018/0360760 A1 | 12/2018 | Mckinney et al. |
| 2019/0029972 A1 | 1/2019 | Dong et al. |
| 2019/0076472 A1 | 3/2019 | Thompson |
| 2019/0110992 A1 | 4/2019 | Stomberg et al. |
| 2019/0133924 A1 | 5/2019 | Hamed |
| 2019/0151294 A1 | 5/2019 | Iwaki |
| 2019/0183883 A1 | 6/2019 | Mckinney et al. |
| 2019/0185562 A1 | 6/2019 | Gromada et al. |
| 2019/0216779 A1 | 7/2019 | Basta et al. |
| 2019/0224193 A1 | 7/2019 | Reid et al. |
| 2019/0231772 A1 | 8/2019 | Bear et al. |
| 2019/0231852 A1 | 8/2019 | Cowley et al. |
| 2019/0282508 A1 | 9/2019 | Shah et al. |
| 2019/0307691 A1 | 10/2019 | Gaillard et al. |
| 2019/0343829 A1 | 11/2019 | Bear et al. |
| 2019/0350858 A1 | 11/2019 | Wittorff |
| 2019/0350867 A1 | 11/2019 | Hahn |
| 2019/0358222 A1 | 11/2019 | Flanagan et al. |
| 2019/0388354 A1 | 12/2019 | Odidi |
| 2020/0030242 A1 | 1/2020 | Bonner et al. |
| 2020/0113901 A1 | 4/2020 | Campbell et al. |
| 2020/0121595 A1 | 4/2020 | Zhao et al. |
| 2020/0138704 A1 | 5/2020 | Wan et al. |
| 2020/0138705 A1 | 5/2020 | Wan et al. |

(56) References Cited

U.S. PATENT DOCUMENTS

| | | |
|---|---|---|
| 2020/0157168 A1 | 5/2020 | Riber et al. |
| 2020/0197388 A1 | 6/2020 | Bear et al. |
| 2020/0306463 A1 | 10/2020 | Shahaf et al. |
| 2020/0338025 A1 | 10/2020 | Dandiker et al. |
| 2020/0361941 A1 | 11/2020 | Martin et al. |
| 2021/0046259 A1 | 2/2021 | Hasegawa et al. |
| 2021/0059944 A1 | 3/2021 | Scheer et al. |
| 2021/0077415 A1 | 3/2021 | Liang et al. |
| 2021/0171499 A1 | 6/2021 | Ammann et al. |
| 2021/0228488 A1 | 7/2021 | Pilgaonkar et al. |
| 2021/0251977 A1 | 8/2021 | McCarty |
| 2021/0267968 A1 | 9/2021 | Mckinney et al. |
| 2021/0275536 A1 | 9/2021 | Bentz |
| 2021/0283126 A1 | 9/2021 | Dunayevich et al. |
| 2021/0290557 A1 | 9/2021 | Huang et al. |
| 2021/0299119 A1 | 9/2021 | Dunayevich et al. |
| 2021/0338678 A1 | 11/2021 | Zablow |
| 2021/0346469 A1 | 11/2021 | Cowley et al. |
| 2021/0354984 A1 | 11/2021 | Langer et al. |
| 2022/0051775 A1 | 2/2022 | Rao |
| 2022/0073583 A1 | 3/2022 | Riber et al. |
| 2022/0088007 A1 | 3/2022 | Flanagan et al. |
| 2022/0098313 A1 | 3/2022 | Oral et al. |
| 2022/0105087 A1 | 4/2022 | Flanagan et al. |
| 2022/0112293 A1 | 4/2022 | Gromada et al. |
| 2022/0170019 A1 | 6/2022 | Lhamyani et al. |
| 2022/0177449 A1 | 6/2022 | Brizgys et al. |
| 2022/0184114 A1 | 6/2022 | Lotta et al. |
| 2022/0192993 A1 | 6/2022 | First |
| 2022/0193104 A1 | 6/2022 | Sun et al. |
| 2022/0202808 A1 | 6/2022 | Weber et al. |
| 2022/0208327 A1 | 6/2022 | Klassen et al. |
| 2022/0233520 A1 | 7/2022 | Flanagan et al. |
| 2022/0249505 A1 | 8/2022 | Bentz |
| 2022/0257591 A1 | 8/2022 | Tollefson |
| 2022/0280641 A1 | 9/2022 | Gromad et al. |
| 2022/0287975 A1 | 9/2022 | Kirkpatrick |
| 2022/0287992 A1 | 9/2022 | Kirkpatrick |
| 2022/0298148 A1 | 9/2022 | Brizgys et al. |
| 2022/0306614 A1 | 9/2022 | Brizgys et al. |
| 2022/0313726 A1 | 10/2022 | Lotta et al. |
| 2022/0313789 A1 | 10/2022 | Cone et al. |
| 2022/0378741 A1 | 12/2022 | Choi et al. |
| 2022/0409557 A1 | 12/2022 | Swanson |
| 2022/0409830 A1 | 12/2022 | Shahaf et al. |
| 2023/0002377 A1 | 1/2023 | Liu et al. |
| 2023/0021705 A1 | 1/2023 | Armstrong et al. |
| 2023/0051463 A1 | 2/2023 | Hojgaard et al. |
| 2023/0084144 A1 | 3/2023 | Liu et al. |
| 2023/0102927 A1 | 3/2023 | Armstrong et al. |
| 2023/0174613 A1 | 6/2023 | Bowrey et al. |
| 2023/0218596 A1 | 7/2023 | Parkin et al. |
| 2023/0248716 A1 | 8/2023 | Liu et al. |
| 2023/0266340 A1 | 8/2023 | Flores et al. |
| 2023/0293722 A1 | 9/2023 | Vitaliano et al. |
| 2023/0301922 A1 | 9/2023 | Mckinney et al. |
| 2023/0358765 A1 | 11/2023 | Acosta et al. |
| 2023/0372328 A1 | 11/2023 | Chalamuri et al. |
| 2023/0390385 A1 | 12/2023 | Cowan |
| 2024/0024355 A1 | 1/2024 | Pandey et al. |
| 2024/0041803 A1 | 2/2024 | Lyu et al. |
| 2024/0075043 A1 | 3/2024 | Bentz |
| 2024/0122859 A1 | 4/2024 | Bothra et al. |
| 2024/0141010 A1 | 5/2024 | Riber et al. |
| 2024/0153638 A1 | 5/2024 | Zheng et al. |
| 2024/0158382 A1 | 5/2024 | Shafeev et al. |
| 2024/0158497 A1 | 5/2024 | Gromada et al. |
| 2024/0165020 A1 | 5/2024 | Zhao et al. |
| 2024/0173571 A1 | 5/2024 | Liu et al. |
| 2024/0182973 A1 | 6/2024 | Lotta et al. |
| 2024/0199580 A1 | 6/2024 | Brizgys et al. |
| 2024/0199589 A1 | 6/2024 | Armstrong et al. |
| 2024/0252528 A1 | 8/2024 | Lotta et al. |
| 2024/0252593 A1 | 8/2024 | Camilleri et al. |
| 2024/0282425 A1 | 8/2024 | Low |
| 2024/0299292 A1 | 9/2024 | Wan et al. |
| 2024/0366513 A1 | 11/2024 | Mckinney et al. |
| 2024/0374587 A1 | 11/2024 | Takemoto et al. |
| 2024/0390364 A1 | 11/2024 | Reid et al. |

FOREIGN PATENT DOCUMENTS

| | | |
|---|---|---|
| WO | 2021191268 A1 | 9/2021 |
| WO | 2021245605 A1 | 12/2021 |
| WO | 2022074681 A1 | 4/2022 |
| WO | 2022120444 A1 | 6/2022 |
| WO | 2022154687 A1 | 7/2022 |
| WO | 2022219573 A2 | 10/2022 |
| WO | 2022222971 A1 | 10/2022 |
| WO | 2023055939 A1 | 4/2023 |
| WO | 2023174910 A1 | 9/2023 |
| WO | 2024088808 A1 | 5/2024 |
| WO | 2024130044 A1 | 6/2024 |

OTHER PUBLICATIONS

PCT International Search Report and Written Opinion in PCT/US2025/029954 dated Oct. 10, 2025, 24 pages.

Altaf, S. A.; Hoag, S. W.; Ayres, J. W., "Bead compacts. I. Effect of compression on maintenance of polymer coat integrity multilayered bead formulations," Drug Development and Industrial Pharmacy, vol. 24, No. 8, pp. 737-746, Aug. 1998.

Non-Final Office Action in U.S. Appl. No. 18/917,080, dated Jan. 30, 2025, 71 pages.

* cited by examiner

—◆— B1 (6.8% total wt gain/Polymer wt gain = 4.3%)
—◆— B2 (8.1% total wt gain/Polymer wt gain = 5.1%)
········ B3 (9.5% total wt gain/Polymer wt gain = 6%)
—◆— B4 (12.2% total wt gain/Polymer wt gain = 7.7%)

--------- B5 (8.2% total wt gain/ 6% polymer wt gain) (Organic EC coating system) (10% plasticizer)
---◆--- B7 (17.6% total wt gain/13% polymer wt gain) (Organic EC coating system) (10% plasticizer)
.........⬛....... B8 (11.1% total wt gain/7% polymer wt gain) (Aqueous EC coating system) (21.3% plasticizer)
━━◆━━ B9 (20.5% total wt gain/13% polymer wt gain) (Aqueous EC coating system) (21.3% plasticizer)

B5 (8.2% total wt gain/ 6% polymer wt gain)
B12 (5.4% total wt gain/4% polymer wt gain)
B13 (6.8% total wt gain/5% polymer wt gain)
B14 (8.1% total wt gain/6% polymer wt gain)

PHARMACEUTICAL FORMULATIONS COMPRISING NALTREXONE AND/OR BUPROPION

CROSS-REFERENCE TO RELATED APPLICATIONS

This application is a divisional of application Ser. No. 18/917,080, filed Oct. 16, 2024. The disclosures of all applications cited in this paragraph are incorporated herein in their entirety by reference.

TECHNICAL FIELD

The present disclosure generally relates to pharmaceutical formulations comprising naltrexone and/or bupropion.

BACKGROUND

CONTRAVE® (naltrexone hydrochloride and bupropion hydrochloride) extended-release tablets is currently indicated as an adjunct to a reduced-calorie diet and increased physical activity for chronic weight management in adults with an initial body mass index (BMI) of: 30 kg/m$^2$ or greater (obese); or 27 kg/m$^2$ or greater (overweight) in the presence of at least one weight-related comorbidity (e.g., hypertension, type 2 diabetes mellitus, or dyslipidemia). However, there is a need for new formulations of naltrexone and/or bupropion for the treatment of disorders such as overweight or obesity.

SUMMARY

One aspect of the present disclosure relates to an extended-release, multilayer particulate (e.g. bead) comprising naltrexone or a salt thereof. In various embodiments of this aspect, the extended-release, multilayer bead comprises: a core particle, wherein the core particle is drug-free; an optional seal coating coated on the surface of the core particle; a drug layer comprising naltrexone, or a salt thereof, coated on the surface of the core particle or, when present, the seal coating; a non-aqueous barrier coating coated on the surface of the drug layer; an extended release coating coated on the surface of the barrier coating; and an optional top coating coated on the surface of the extended release coating.

In one or more embodiments, the naltrexone-containing bead has an average diameter of about 500-900 μm, such as about 600-750 μm.

In one or more embodiments, the naltrexone is present in the drug layer as the hydrochloride salt. In one or more embodiments, the naltrexone comprises an anhydrous polymorph of the hydrochloride salt (Form L). In one or more embodiments, the naltrexone hydrochloride comprises an ethanol solvate (Form F). In one or more embodiments, the naltrexone hydrochloride comprises an anhydrous polymorph (Form L) and/or an ethanol solvate (Form F). In one or more embodiments, the naltrexone hydrochloride comprises greater than 99% Form L and less than 1% Form F. In one or more embodiments, the naltrexone hydrochloride is substantially free of amorphous naltrexone hydrochloride.

In one or more embodiments, the drug layer comprises about 50% to about 95% of naltrexone, or a salt thereof. In one or more embodiments, the extended-release, multilayer bead comprises about 10% to about 80% of naltrexone, or a salt thereof.

In one or more embodiments, the drug-free core particle is selected from a microcrystalline cellulose particle, a silica particle, and a sugar particle. In one or more embodiments, the drug-free core particle is a microcrystalline cellulose particle.

In one or more embodiments, the drug-free core particle is spherical. In one or more embodiments, the drug-free core particle has an average diameter of 200-800 μm, such as 350-500 μm.

In one or more embodiments, the drug layer further comprises a low viscosity binder. In one or more embodiments, the binder is selected from Hypromellose 3 cps, Hypromellose 5 cps, and Hydroxypropyl cellulose. In one or more embodiments, the binder is Hydroxypropyl cellulose Klucel EXF. In one or more embodiments, the ratio of naltrexone, or a salt thereof, to binder is about 100:1 to about 10:1.

In one or more embodiments, the non-aqueous barrier coating comprises a low viscosity binder. In one or more embodiments, the binder is selected from Hypromellose 3 cps, Hypromellose 5 cps, and Hydroxypropyl cellulose. In one or more embodiments, the binder is Hydroxypropyl cellulose Klucel EXF.

In one or more embodiments, the non-aqueous barrier coating is prepared under anhydrous conditions. In one or more embodiments, the non-aqueous barrier coating is prepared using a solvent selected from the group consisting of Class 3 solvents. In one or more embodiments, the solvent is selected from acetic acid, acetone, ethanol and combinations thereof. In one or more embodiments, the solvent comprises dehydrated ethanol.

In one or more embodiments, the extended-release coating achieves a mean peak naltrexone concentration ($C_{max}$) of about 1.4 ng/mL, a time to peak concentration ($T_{max}$) of about 2 hours, and/or an extent of exposure ($AUC_{0-inf}$) of about 8.4 ng·hr/mL after administration of a plurality of the extended-release multilayer beads having a total naltrexone loading of about 16 mg.

In one or more embodiments, the extended-release coating comprises a release controlling polymer and a hydrophilic plasticizer. In one or more embodiments, the release controlling polymer comprises ethyl cellulose. In one or more embodiments, the release controlling polymer is present in an amount of about 5% to about 25% by weight of the extended-release, multilayer bead.

In one or more embodiments, the hydrophilic plasticizer comprises triethyl citrate. In one or more embodiments, the hydrophilic plasticizer is present in an amount of about 0.5% to 5% by weight of the extended-release, multilayer bead. In one or more embodiments, the hydrophilic plasticizer is present in an amount of about 5% to about 15% of dry polymer concentration.

In one or more embodiments, the extended-release coating comprises a pore former. In one or more embodiments, the pore former comprises Hypromellose.

In one or more embodiments, the naltrexone-containing bead maintains naltrexone stability for at least 6, 12, 18 or 24 months at room temperature. In one or more embodiments, the naltrexone-containing bead maintains naltrexone stability under accelerated aging conditions of 40° C./75% relative humidity (RH) for 7, 14 or 28 days or 1, 2, 3, 4, 5, 6 or more months. In one or more embodiments, the naltrexone stability comprises one or more of release stability, impurity/degradant stability and/or polymorphic stability.

In one or more embodiments, the naltrexone-containing bead comprises no more than 0.5% 2-chloro-10α-hydroxynaltrexone, based on the weight of naltrexone.

In one or more embodiments, the naltrexone-containing bead comprises no more than 2% impurities, based on the weight of naltrexone.

Another aspect of the present disclosure relates to extended-release, multilayer particulate (e.g. bead) comprising bupropion or a salt thereof. In various embodiments of this aspect, the extended-release, multilayer bead comprises: a core particle comprising bupropion, or a salt thereof; an optional seal coating coated on the surface of the core particle; an extended-release coating coated on the surface of the core particle, or if present, on the surface of the seal coating; and an optional top coating coated on the surface of the extended-release coating.

In one or more embodiments, the bupropion is present as the hydrochloride salt. In one or more embodiments, the bupropion, or a salt thereof, is micronized (D10=1 μm, D50=6 μm and D90=40 μm). In one or more embodiments, the bupropion, or a salt thereof, has a bulk density of about 0.1 to 0.4 g/cc.

In one or more embodiments, the bupropion-containing core particles comprise ≥70% w/w bupropion, or a salt thereof. In one or more embodiments, the bupropion-containing beads comprise 60 to 80% w/w bupropion, or a salt thereof.

In one or more embodiments, the bupropion-containing core particle is prepared using a pelletization process. In one or more embodiments, the bupropion-containing core particle is prepared using extrusion. In one or more embodiments, the bupropion-containing core particle is prepared using extrusion-spheronization.

In one or more embodiments, the average diameter of the bupropion-containing core particle is about 1000-1500 μm, such as about 1200 μm.

In one or more embodiments, the bupropion-containing bead comprises no more than 3.2% impurities, based on the weight of bupropion. In one or more embodiments, the bupropion-containing bead comprises no more than 1% (2R,3R,5R)-2-(3-chlorophenyl)-2-hydroxy-3-methylthio-morpholine-5-carboxylic acid (RRR-CHMTCA), based on the weight of bupropion. In one or more embodiments, the bupropion-containing bead comprises no more than 0.5% (2S,3S,5R)-2-(3-chlorophenyl)-2-hydroxy-3-methylthio-morpholine-5-carboxylic acid (SSR-CHMTCA), based on the weight of bupropion.

Another aspect of the disclosure relates to an oral dosage form comprising a plurality of the extended-release, multilayer multiparticulates (e.g. beads) comprising naltrexone or salt thereof.

Another aspect of the disclosure relates to an oral dosage form comprising a plurality of the extended-release, multilayer multiparticulates (e.g. beads) comprising bupropion or salt thereof.

Another aspect of the disclosure relates to oral dosage form comprising a plurality of the extended-release, multilayer multiparticulates (e.g. beads) comprising naltrexone or salt thereof and a plurality of the extended-release, multilayer multiparticulates (e.g. beads) comprising bupropion or salt thereof.

In various aspects, the dosage form has an in vitro bupropion dissolution profile in a dissolution test of USP Apparatus 1 Basket Method at 100 rpm in a dissolution medium of water at 37° C. of: less than 30% of the bupropion released in one hour; and/or less than 60% of the bupropion released in two hours.

In various aspects, the dosage form has an in vitro naltrexone dissolution profile in a dissolution test of USP Apparatus 1 Basket Method at 100 rpm in a dissolution medium of water at 37° C. of: less than 30% of the naltrexone released in one hour; and/or less than 60% of the naltrexone released in two hours.

Another aspect of the present disclosure relates to an oral dosage form comprising a naltrexone extended-release formulation comprising about 8 to about 32 mg of naltrexone or a salt thereof; and a bupropion extended-release formulation comprising about 90 mg to about 360 mg of bupropion or a salt thereof. In various embodiments of this aspect, the bupropion extended-release formulation has an in vitro bupropion dissolution profile in a dissolution test of USP Apparatus 1 Basket Method at 100 rpm in a dissolution medium of water at 37° C. of: less than 30% of the bupropion released in one hour; and/or less than 60% of the bupropion released in two hours. In various embodiments of this aspect, the naltrexone extended-release formulation has an in vitro naltrexone dissolution profile in a dissolution test of USP Apparatus 1 Basket Method at 100 rpm in a dissolution medium of water at 37° C. of: less than 30% of the naltrexone released in one hour; and/or less than 60% of the naltrexone released in two hours.

In one or more embodiments, the in vitro naltrexone dissolution profile in the dissolution test is: less than 20% of the naltrexone released in one hour; and/or less than 50% of the naltrexone released in two hours. In one or more embodiments, the in vitro naltrexone dissolution profile in the dissolution test is: 2% to 20% of the naltrexone released in one hour; and/or 10 to 50% of the naltrexone released in two hours; and/or 60% to 90% of the naltrexone released in four hours. In one or more embodiments, the in vitro naltrexone dissolution profile in the dissolution test is: 2% to 10% of the naltrexone released in one hour; and/or 20 to 40% of the naltrexone released in two hours.

In one or more embodiments, the in vitro bupropion dissolution profile in the dissolution test is: less than 20% of the bupropion released in one hour; and/or less than 50% of the bupropion released in two hours. In one or more embodiments, the in vitro bupropion dissolution profile in the dissolution test is: 2% to 20% of the bupropion released in one hour; and/or 10 to 50% of the bupropion released in two hours; and/or 50% to 90% of the bupropion released in four hours. In one or more embodiments, the in vitro bupropion dissolution profile in the dissolution test is: 2% to 10% of the bupropion released in one hour; and/or 20 to 40% of the bupropion released in two hours.

In one or more embodiments, the oral dosage form comprises about 8 mg of naltrexone or salt thereof and about 90 mg of bupropion or salt thereof.

In one or more embodiments, the oral dosage form comprises about 16 mg of naltrexone or salt thereof and about 180 mg of bupropion or salt thereof.

In one or more embodiments, the oral dosage form comprises about 24 mg of naltrexone or salt thereof and about 270 mg of bupropion or salt thereof.

In one or more embodiments, the oral dosage form comprises about 32 mg of naltrexone or salt thereof and about 360 mg of bupropion or salt thereof.

In one or more embodiments, administration of the oral dosage form comprising 32 mg of naltrexone to a group of subjects at steady state provides an average maximum naltrexone plasma concentration $C_{max}$ of 0.8 to 2.3 ng/mL, such as 1.1 to 1.8 ng/mL.

In one or more embodiments, administration of the oral dosage form comprising 32 mg of naltrexone to a group of subjects at steady state provides an average naltrexone plasma area under the curve $AUC_{0-24h}$ of 10 to 28 ng*h/mL, such as 13 to 22 ng*h/mL.

In one or more embodiments, administration of the oral dosage form comprising 360 mg of bupropion to a group of subjects at steady state provides an average maximum bupropion plasma concentration $C_{max}$ of 120 to 330 ng/mL, such as 150 to 260 ng/mL.

In one or more embodiments, administration of the oral dosage form comprising 360 mg of bupropion to a group of subjects at steady state provides an average bupropion plasma area under the curve $AUC_{0-24h}$ of 1,700 to 4,500 ng*h/mL, such as 2,200 to 3,600 ng*h/mL.

In one or more embodiments, the naltrexone salt is naltrexone hydrochloride. In one or more embodiments, the naltrexone comprises an anhydrous polymorph of the hydrochloride salt (Form L). In one or more embodiments, the naltrexone hydrochloride comprises an ethanol solvate (Form F). In one or more embodiments, the naltrexone hydrochloride comprises an anhydrous polymorph (Form L) and/or an ethanol solvate (Form F). In one or more embodiments, the naltrexone hydrochloride comprises greater than 99% Form L and less than 1% Form F. In one or more embodiments, the naltrexone hydrochloride is substantially free of amorphous naltrexone hydrochloride.

In one or more embodiments, the oral dosage form, when administered to a human subject once daily, is bioequivalent to a US FDA-approved trilayer tablet dosage form comprising naltrexone hydrochloride and bupropion hydrochloride (e.g. CONTRAVE®) administered to a human subject twice daily, under the bioequivalence parameters of: (a) a 90% Confidence Interval for AUC which is between 80% and 125%, and (b) a 90% Confidence Interval for $C_{max}$, which is between 80% and 125%.

Another aspect of the present disclosure relates to an oral dosage form that, when administered to a human subject once daily, is bioequivalent to a US FDA-approved trilayer tablet dosage form comprising naltrexone hydrochloride and bupropion hydrochloride (e.g. CONTRAVE®) administered to a human subject twice daily, under the bioequivalence parameters of: (a) a 90% Confidence Interval for AUC which is between 80% and 125%, and (b) a 90% Confidence Interval for $C_{max}$, which is between 80% and 125%.

In various embodiments of this aspect, the oral dosage form comprises about 8 mg to about 32 mg of naltrexone, or a salt thereof.

In one or more embodiments, the oral dosage form comprises about 90 mg to about 360 mg of bupropion, or a salt thereof In one or more embodiments, the oral dosage form comprises a capsule.

Another aspect of the present disclosure relates to a method of administering naltrexone and/or bupropion by administering an oral dosage form as described herein.

Another aspect of the present disclosure relates to a method of treating overweight or obesity by administering an oral dosage form as described herein.

In one or more embodiments, the method comprises administering a first oral dosage form comprising about 8 mg of naltrexone or salt thereof and about 90 mg of bupropion or salt thereof, wherein the first oral dosage form is administered once a day for a first week; administering a second oral dosage form comprising about 16 mg of naltrexone or salt thereof and about 180 mg of bupropion or salt thereof, wherein the second oral dosage form is administered once a day for a second week; administering a third oral dosage form comprising about 24 mg of naltrexone or salt thereof and about 270 mg of bupropion or salt thereof, wherein the third oral dosage form is administered once a day for a third week; and administering a fourth oral dosage form comprising about 32 mg of naltrexone or salt thereof and about 360 mg of bupropion or salt thereof, wherein the fourth oral dosage form is administered once a day for a fourth and subsequent weeks.

DETAILED DESCRIPTION

Figure 1:
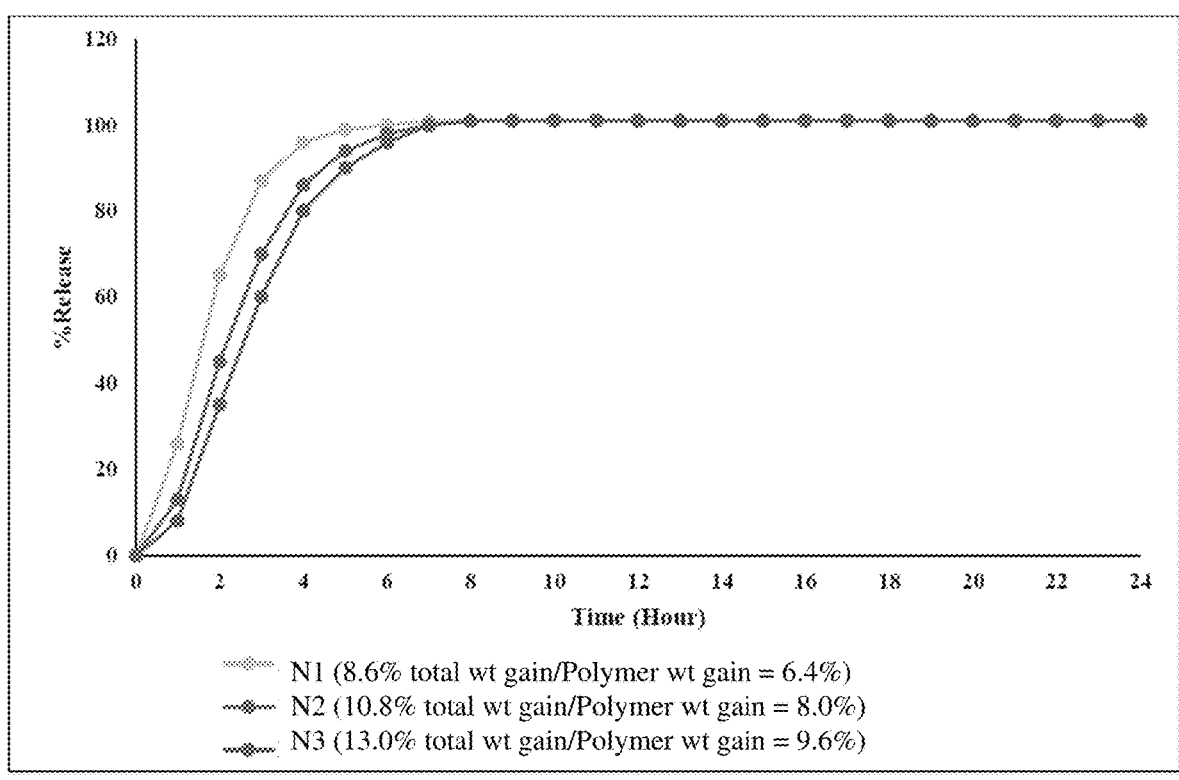
FIG. 1 shows the in vitro dissolution profiles of various naltrexone extended-release formulations.

Various aspects of the present disclosure relate to methods and pharmaceutical formulations comprising naltrexone and/or bupropion. In one or more embodiments, the methods and formulations described herein overcome challenges that are unique to naltrexone, bupropion and/or the combination of naltrexone and bupropion. For example, it has been found that (1) naltrexone and bupropion should be physically separated to prevent potential interaction between the two active ingredients; (2) naltrexone hydrochloride is highly hygroscopic and readily converts between different polymorphs/solvates; (3) amorphous naltrexone hydrochloride is not chemically stable and subject to rapid degradation; (4) bupropion dosages commonly prescribed in combination with naltrexone (e.g. 360 mg/day) are relatively high loadings of drug to incorporate into extended-release formulations; and (5) bupropion dosages commonly prescribed in combination with naltrexone (e.g. 360 mg/day) are more than ten times the corresponding naltrexone dosages (e.g. 32 mg/day).

CONTRAVE® (naltrexone hydrochloride and bupropion hydrochloride) extended-release tablets is currently indicated as an adjunct to a reduced-calorie diet and increased physical activity for chronic weight management in adults with an initial body mass index (BMI) of: 30 kg/m² or greater (obese); or 27 kg/m² or greater (overweight) in the presence of at least one weight-related comorbidity (e.g., hypertension, type 2 diabetes mellitus, or dyslipidemia). In various embodiments, the pharmaceutical formulations described herein can also be used for the treatment of overweight or obesity. The prescribing information for CONTRAVE® is hereby incorporated by reference in its entirety.

As used herein, the phrase "US FDA-approved trilayer tablet dosage form comprising naltrexone hydrochloride and bupropion hydrochloride" refers to the trilayer tablet dosage form of CONTRAVE® (naltrexone hydrochloride and bupropion hydrochloride) that was first approved by the US Food and Drug Administration on Sep. 10, 2014, and is currently available as of Oct. 15, 2024 in the US by prescription.

Exemplary doses, dosage forms, formulations and methods of administering naltrexone and bupropion are described in the following patents and patent applications, which are hereby incorporated by reference in their entireties: U.S. Pat. Nos. 7,375,111; 8,916,195; 8,088,786; 8,722,085; 8,815, 889; 9,248,123; 9,633,575; 8,969,371; 10,231,962; 11,324, 741; U.S. Pat. App. Pub. No. 2011/0028505; U.S. Pat. App. Pub. No. 2013/0252995 and U.S. Pat. App. Pub. No. 2013/ 0245056.

In some embodiments, the naltrexone and/or bupropion (or salt(s) thereof) is administered once per day. In one or more embodiments, naltrexone and bupropion (or salt(s) thereof) are administered in a single oral dosage form once per day.

In some embodiments, the daily dose of naltrexone can range from about 8 mg to about 32 mg. In some embodiments, the daily dose is about 8 mg, about 16 mg, about 24 mg, or about 32 mg of naltrexone, or a range defined by any two of the preceding values. In one or more embodiments, the naltrexone or pharmaceutically acceptable salt thereof is administered at a dose of about 8 mg per day. In one or more embodiments, the naltrexone or pharmaceutically acceptable salt thereof is administered at a dose of about 16 mg per day. In one or more embodiments, the naltrexone or pharmaceutically acceptable salt thereof is administered at a dose of about 24 mg per day. In one or more embodiments, the naltrexone or pharmaceutically acceptable salt thereof is administered at a dose of about 32 mg per day.

In some embodiments, the daily dose of bupropion can range from about 90 mg to about 360 mg. In some embodiments, the daily dose is about 90 mg, about 180 mg, about 270 mg, or about 360 mg of bupropion, or a range defined by any two of the preceding values. In one or more embodiments, the bupropion or pharmaceutically acceptable salt thereof is administered at a dose of about 90 mg per day. In one or more embodiments, the bupropion or pharmaceutically acceptable salt thereof is administered at a dose of about 180 mg per day. In one or more embodiments, the bupropion or pharmaceutically acceptable salt thereof is administered at a dose of about 270 mg per day. In one or more embodiments, the bupropion or pharmaceutically acceptable salt thereof is administered at a dose of about 360 mg per day.

The compositions described herein may be distributed, provided to a patient for self-administration, or administered to an individual.

In some embodiments, that naltrexone and/or bupropion is provided or administered as an oral dosage form. In some embodiments, the oral dosage form is in the form of a pill, tablet, core, capsule, caplet, loose powder, solution, or suspension. In a preferred embodiment, the oral dosage form is in the form of a pill, tablet, or capsule. In some embodiments, the combined naltrexone/bupropion therapy is provided in a single oral dosage form. In some embodiments, the combined naltrexone/bupropion therapy is provided in a capsule comprising multilayer, extended-release multiparticulates (e.g. beads). As used herein, the term "bead" refers to a particulate comprising the listed components. The bead does not necessarily need to be spherical, but can be any regular or irregular shaped particle. In some embodiments, the bead has a substantially ellipsoid shape. In some embodiments, the bead is substantially spherical.

In various embodiments, the naltrexone or salt thereof is provided in multilayer, extended-release beads. In one or more embodiments, the extended-release, multilayer bead comprises: a core particle, wherein the core particle is drug-free; an optional seal coating coated on the surface of the core particle; a drug layer comprising naltrexone, or a salt thereof, coated on the surface of the core particle or, when present, the seal coating; a non-aqueous barrier coating coated on the surface of the drug layer; an extended release coating coated on the surface of the barrier coating; and an optional top coating coated on the surface of the extended release coating.

In one or more embodiments, the drug layer comprises about 50% to about 95% of naltrexone, or a salt thereof. In various embodiments, the drug layer comprises at least 50%, 55%, 60%, 65%, 70%, 75% or 80% by weight naltrexone, or salt thereof. In various embodiments, the drug layer comprises less than 99%, 98%, 97%, 96%, 95%, 94%, 93%, 92%, 91%, 90% or 85% by weight naltrexone, or salt thereof.

In one or more embodiments, the extended-release, multilayer bead comprises about 10% to about 80% of naltrexone, or a salt thereof. In various embodiments, the extended-release, multilayer bead comprises at least 10%, 15%, 20%, 25 or 30% by weight naltrexone, or salt thereof. In various embodiments, the extended-release, multilayer bead comprises less than 50%, 45%, 40%, 35%, 30% or 25% by weight naltrexone, or salt thereof.

In one or more embodiments, the drug-free core particle for the naltrexone-containing bead is selected from a microcrystalline cellulose particle, a silica particle, and a sugar particle. In one or more embodiments, the drug-free core particle is a microcrystalline cellulose particle.

In one or more embodiments, the drug-free core particle for the naltrexone-containing bead is spherical. In one or more embodiments, the drug-free core particle has an average diameter of 200-800 μm, such as 350-500 μm.

In one or more embodiments, the drug layer for the naltrexone-containing bead further comprises a low viscosity binder. In one or more embodiments, the binder is selected from Hypromellose 3 cps, Hypromellose 5 cps, and Hydroxypropyl cellulose. In one or more embodiments, the binder is Hydroxypropyl cellulose Klucel EXF. In one or more embodiments, the weight ratio of naltrexone, or a salt thereof, to binder is about 100:1 to about 10:1, such as about 100:1, about 90:1, about 80:1, about 70:1, about 60:1, about 50:, about 40:1, about 30:1, about 25:1, about 20:1, about 15:1 or about 10:10.

In one or more embodiments, the drug layer comprising naltrexone is applied to the drug-free core particle under anhydrous conditions. In one or more embodiments, the drug layer is prepared using a solvent selected from the group consisting of Class 3 solvents. In one or more embodiments, the solvent is selected from acetic acid, acetone, ethanol and combinations thereof. In one or more embodiments, the solvent comprises dehydrated ethanol.

In one or more embodiments, the non-aqueous barrier coating comprises a low viscosity binder. In one or more embodiments, the binder is selected from Hypromellose 3 cps, Hypromellose 5 cps, and Hydroxypropyl cellulose. In one or more embodiments, the binder is Hydroxypropyl cellulose Klucel EXF.

In one or more embodiments, the non-aqueous barrier coating is prepared under anhydrous conditions. In one or more embodiments, the non-aqueous barrier coating is prepared using a solvent selected from the group consisting of Class 3 solvents. In one or more embodiments, the solvent is selected from acetic acid, acetone, ethanol and combinations thereof. In one or more embodiments, the solvent comprises dehydrated ethanol.

In one or more embodiments, the extended-release coating for the naltrexone-containing bead achieves a mean peak naltrexone concentration ($C_{max}$) of about 1.4 ng/mL, a time to peak concentration ($T_{max}$) of about 2 hours, and/or an extent of exposure ($AUC_{0-inf}$) of about 8.4 ng·hr/mL after administration of a plurality of the extended-release multilayer beads having a total naltrexone loading of about 16 mg.

In one or more embodiments, the extended-release coating comprises a release controlling polymer and a hydrophilic plasticizer. In one or more embodiments, the release controlling polymer comprises ethyl cellulose. In one or more embodiments, the wherein the release controlling polymer is present in an amount of about 5% to about 25% by weight of the extended-release, multilayer bead.

In one or more embodiments, the hydrophilic plasticizer comprises triethyl citrate. In one or more embodiments, the hydrophilic plasticizer is present in an amount of about 0.5% to 5% by weight of the extended-release, multilayer bead. In one or more embodiments, the hydrophilic plasticizer is present in an amount of about 5% to about 15% of dry polymer concentration.

In one or more embodiments, the extended-release coating comprises a pore former. In one or more embodiments, the pore former comprises Hypromellose. In one or more embodiments, the pore former is present in an amount of about 10% to about 40% of the release controlling polymer, such as about 10%, about 15%, about 20%, about 25%, about 30%, about 35% or about 40%.

In one or more embodiments, the naltrexone-containing bead maintains naltrexone stability for at least 6, 12, 18 or 24 months at room temperature. In one or more embodiments, the naltrexone-containing bead maintains naltrexone stability under accelerated aging conditions of 40° C./75% relative humidity (RH) for 7, 14 or 28 days or 1, 2, 3, 4, 5, 6 or more months. In one or more embodiments, the naltrexone stability comprises one or more of release stability, impurity/degradant stability and/or polymorphic stability.

In one or more embodiments, the naltrexone-containing bead comprises no more than 2% impurities, based on the weight of naltrexone. In one or more embodiments, the naltrexone-containing bead comprises no more than 0.5% 2-chloro-10α-hydroxynaltrexone, based on the weight of naltrexone.

In one or more embodiments, the naltrexone salt comprises naltrexone hydrochloride. In one or more embodiments, the naltrexone hydrochloride comprises an anhydrous polymorph of the hydrochloride salt (Form L). In one or more embodiments, the naltrexone hydrochloride comprises an ethanol solvate of the hydrochloride salt (Form F). In one or more embodiments, the naltrexone hydrochloride comprises an anhydrous polymorph (Form L) and/or an ethanol solvate (Form F). In one or more embodiments, the naltrexone hydrochloride comprises greater than 90%, 95%, 99%, or 99.5% Form L and less than 10%, 5%, 1% or 0.5% Form F. In one or more embodiments, the naltrexone hydrochloride has an X-Ray powder diffractogram (XRPD) that is consistent with Form L. In one or more embodiments, the naltrexone hydrochloride has an XRPD that is consistent with Form F. In one or more embodiments, the naltrexone hydrochloride has an XRPD that is consistent with Forms F and L. In one or more embodiments, the naltrexone hydrochloride is substantially free of amorphous naltrexone hydrochloride.

In various embodiments, the bupropion or salt thereof is provided in multilayer, extended-release beads. In one or more embodiments, the extended-release, multilayer bead comprises: a core particle comprising bupropion, or a salt thereof; an optional seal coating coated on the surface of the core particle; an extended-release coating coated on the surface of the core particle, or if present, on the surface of the seal coating; and an optional top coating coated on the surface of the extended-release coating.

In one or more embodiments, the bupropion is present as the hydrochloride salt. In one or more embodiments, the bupropion, or a salt thereof, is micronized (D10=1 μm, D50=6 μm and D90=40 μm). In one or more embodiments, the bupropion, or a salt thereof, has a bulk density of about 0.1 to 0.4 g/cc.

In one or more embodiments, the bupropion-containing core particles comprise ≥70% w/w bupropion, or a salt thereof. In one or more embodiments, the core particles comprise at least 60%, 65%, 70%, 75%, 80% or 85% by weight bupropion, or a salt thereof. In one or more embodiments, the core particles comprise less than 95%, 90%, 85% or 80% by weight bupropion, or a salt thereof.

In one or more embodiments, the bupropion-containing beads comprise 60 to 80% w/w bupropion, or a salt thereof. In one or more embodiments, the core particles comprise at least 40%, 45%, 50%, 55%, 60% or 65% by weight bupropion, or a salt thereof. In one or more embodiments, the core particles comprise less than 95%, 90%, 85%, 80%, 75% or 70% by weight bupropion, or a salt thereof.

In one or more embodiments, the bupropion-containing core particle is prepared using a pelletization process. In one or more embodiments, the bupropion-containing core particle is prepared using extrusion. In one or more embodiments, the bupropion-containing core particle is prepared using extrusion-spheronization.

In one or more embodiments, the average diameter of the bupropion-containing core particle is about 1000-1500 μm, such as about 1200 μm.

In one or more embodiments, the bupropion-containing bead comprises no more than 3.2% impurities, based on the weight of bupropion. In one or more embodiments, the bupropion-containing bead comprises no more than 1% (2R,3R,5R)-2-(3-chlorophenyl)-2-hydroxy-3-methylthio-morpholine-5-carboxylic acid (RRR-CHMTCA), based on the weight of bupropion. In one or more embodiments, the bupropion-containing bead comprises no more than 0.5% (2S,3S,5R)-2-(3-chlorophenyl)-2-hydroxy-3-methylthio-morpholine-5-carboxylic acid (SSR-CHMTCA), based on the weight of bupropion.

In one or more embodiments, the bupropion salt comprises bupropion hydrochloride. In one or more embodiments, the bupropion, or a salt thereof, is micronized (D10=1 μm, D50=6 μm and D90=40 μm).

In one or more embodiments, the bupropion, or a salt thereof, has a bulk density of about 0.1 to 0.4 g/cc. In various embodiments, the bulk density is about 0.1, 0.15, 0.2, 0.25, 0.3, 0.35, 0.4 g/cc or a range defined by any two of the preceding values.

In some embodiments, at least one of naltrexone and bupropion is administered with varying amounts during treatment. In some embodiments, the dose of naltrexone and bupropion is administered in an escalating manner. In one or more embodiments, 8 mg of naltrexone (or salt thereof) and 90 mg of bupropion (or salt thereof) are administered daily for a first week. In one or more embodiments, 16 mg of naltrexone (or salt thereof) and 180 mg of bupropion (or salt thereof) are administered daily for a second week. In one or more embodiments, 24 mg of naltrexone (or salt thereof) and 270 mg of bupropion (or salt thereof) are administered daily for a third week. In one or more embodiments, 32 mg of naltrexone (or salt thereof) and 360 mg of bupropion (or salt thereof) are administered daily thereafter.

In some embodiments, at least one of naltrexone or bupropion is in an extended-release formulation. Although specific reference is made to extended-release, multilayer bead formulations, other formulations may be utilized to obtain the dissolution profiles as described herein.

In some embodiments, the naltrexone is in an extended-release formulation. In various embodiments, the naltrexone extended-release formulation has an in vitro naltrexone dissolution profile in a dissolution test of USP Apparatus 1 Basket Method at 100 rpm in a dissolution medium of water at 37° C. of: less than 30% of the naltrexone released in one hour; and/or less than 60% of the naltrexone released in two hours.

In various embodiments, the in vitro naltrexone dissolution profile provides less than 30%, 25%, 20%, 15% or 10% of naltrexone released in one hour. In various embodiments, the in vitro naltrexone dissolution profile provides at least 1%, 2%, 3%, 4%, 5%, 6%, 7%, 8%, 9% or 10% of naltrexone released in one hour.

In various embodiments, the in vitro naltrexone dissolution profile provides less than 60%, 55%, 50%, 45% or 40% of naltrexone released in two hours. In various embodiments, the in vitro naltrexone dissolution profile provides at least 10%, 15%, 20%, 25%, 30%, 35% or 40% of naltrexone released in two hours.

In various embodiments, the in vitro naltrexone dissolution profile provides less than 80%, 75%, 70%, 65% or 60% of naltrexone released in three hours. In various embodiments, the in vitro naltrexone dissolution profile provides at least 30%, 35%, 40%, 45%, 50%, 55% or 60% of naltrexone released in three hours.

In various embodiments, the in vitro naltrexone dissolution profile provides less than 95%, 90%, 85% or 80% of naltrexone released in four hours. In various embodiments, the in vitro naltrexone dissolution profile provides at least 50%, 55%, 60%, 65%, 70%, 75% or 80% of naltrexone released in four hours.

In various embodiments, the in vitro naltrexone dissolution profile provides less than 99%, 98%, 97%, 96%, 95%, 94%, 93%, 92%, 91% or 90% of naltrexone released in five hours. In various embodiments, the in vitro naltrexone dissolution profile provides at least 60%, 65%, 70%, 75%, 80%, 85% or 90% of naltrexone released in five hours.

In various embodiments, the in vitro naltrexone dissolution profile provides less than 99%, 98%, 97%, 96%, 95%, 94%, 93%, 92%, 91% or 90% of naltrexone released in six hours. In various embodiments, the in vitro naltrexone dissolution profile provides at least 80%, 85%, 90%, 91%, 92%, 93%, 94%, 95%, 96% or 97% of naltrexone released in six hours.

In some embodiments, the bupropion is in an extended-release formulation. In various embodiments, the bupropion extended-release formulation has an in vitro bupropion dissolution profile in a dissolution test of USP Apparatus 1 Basket Method at 100 rpm in a dissolution medium of water at 37° C. of: less than 30% of the bupropion released in one hour; and/or less than 60% of the bupropion released in two hours.

In various embodiments, the in vitro bupropion dissolution profile provides less than 30%, 25%, 20%, 15% or 10% of bupropion released in one hour. In various embodiments, the in vitro bupropion dissolution profile provides at least 1%, 2%, 3%, 4%, 5%, 6%, 7%, 8%, 9%, 10%, 11%, 12%, 13%, 14% or 15% of bupropion released in one hour.

In various embodiments, the in vitro bupropion dissolution profile provides less than 60%, 55%, 50%, 45%, 40% or 35% of bupropion released in two hours. In various embodiments, the in vitro bupropion dissolution profile provides at least 10%, 15%, 20%, 25%, 30%, 35% or 40% of bupropion released in two hours.

In various embodiments, the in vitro bupropion dissolution profile provides less than 80%, 75%, 70%, 65%, 60%, 55% or 50% of bupropion released in three hours. In various embodiments, the in vitro bupropion dissolution profile provides at least 20%, 25%, 30%, 35%, 40%, 45%, 50% or 55% of bupropion released in three hours.

In various embodiments, the in vitro bupropion dissolution profile provides less than 95%, 90%, 85%, 80%, 75%, 70%, 65% or 60% of bupropion released in four hours. In various embodiments, the in vitro bupropion dissolution profile provides at least 40%, 45%, 50%, 55%, 60%, 65% or 70% of bupropion released in four hours.

In various embodiments, the in vitro bupropion dissolution profile provides less than 99%, 98%, 97%, 96%, 95%, 94%, 93%, 92%, 91%, 90%, 85%, 80%, 75% or 70% of bupropion released in five hours. In various embodiments, the in vitro bupropion dissolution profile provides at least 50%, 55%, 60%, 65%, 70%, 75%, 80%, 85% or 90% of bupropion released in five hours.

In various embodiments, the in vitro bupropion dissolution profile provides less than 99%, 98%, 97%, 96%, 95%, 94%, 93%, 92%, 91%, 90%, 85%, 80% or 75% of bupropion released in six hours. In various embodiments, the in vitro bupropion dissolution profile provides at least 60%, 65%, 70%, 75%, 80%, 85%, 90%, 91%, 92%, 93%, 94%, 95%, 96% or 97% of bupropion released in six hours.

In various embodiments, the release profiles of naltrexone and/or bupropion are achieved through the use of an extended-release coating. In one or more embodiments, the extended-release coating comprises a release controlling polymer. In one or more embodiments, the extended-release coating further comprises a pore former. Incorporation of higher amounts of pore former in the extended-release coating led to faster release rates. Utilization of thicker extended-release coatings (higher polymer weight gain) for the beads lead to slower release rates. Thus, in one or mor embodiments, the release rate of naltrexone and/or bupropion can be varied by incorporating varying thickness/polymer weight gain and/or varying pore former content.

In some embodiments, naltrexone and bupropion are administered individually. In some embodiments, naltrexone and bupropion are administered in a single pharmaceutical composition comprising naltrexone and bupropion. In some embodiments, at least one of naltrexone or bupropion is administered with a physiologically acceptable carrier, diluent, or excipient, or a combination thereof. Reference herein to the use or administration of naltrexone and naltrexone/bupropion combinations is understood to include all modes of administration disclosed or referred to herein, including without limitation separate administration, administration in a single dosage form, administration in the form of salts, and/or metabolites, and/or administration in sustained release forms. Techniques for formulation and administration of the compounds of the instant application may be found in "Remington's Pharmaceutical Sciences," Mack Publishing Co., Easton, Pa., 18th edition, 1990, which is incorporated herein by reference in its entirety.

In some embodiments, naltrexone is administered prior to bupropion. In some embodiments, naltrexone is administered subsequent to bupropion. In some embodiments, naltrexone and bupropion are co-administered. As used herein, co-administration includes administration in a single dosage form, or separate dosage forms that are administered at, or nearly at, the same time.

In one or more embodiments, administration of the oral dosage form comprising 16 mg of naltrexone provides a mean peak naltrexone concentration ($C_{max}$) of about 1.4 ng/mL, a time to peak concentration ($T_{max}$) of about 2 hours, and/or an extent of exposure ($AUC_{0-inf}$) of about 8.4 ng·hr/mL.

In one or more embodiments, the oral dosage form described herein the administered to a group of subjects. In various embodiments, the group of subjects is at least 10, 15, 20, 25, 30, 40, 50, 60, 70, 80, 90 or 100 or more subjects. In various embodiments, the oral dosage form is repeatedly administered to the patients until the subjects reach steady state, which is when the drug absorption and drug elimination between successive administrations are approximately equal.

In one or more embodiments, administration of the oral dosage form comprising 32 mg of naltrexone to a group of subjects at steady state provides an average maximum naltrexone plasma concentration $C_{max}$ of 0.8 to 2.3 ng/mL, such as 1.1 to 1.8 ng/mL. Exemplary naltrexone $C_{max}$ values include those greater than or equal to 0.8, 0.9, 1.0, 1.1, 1.2 or 1.3 ng/mL and/or those less than or equal to 2.3, 2.2, 2.1, 2, 1.9, 1.8, 1.7, 1.6 and 1.5 ng/mL.

In one or more embodiments, administration of the oral dosage form comprising 32 mg of naltrexone a group of subjects at steady state provides an average naltrexone plasma area under the curve $AUC_{0-24h}$ of 10 to 28 ng*h/mL, such as 13 to 22 ng*h/mL. Exemplary naltrexone $AUC_{0-24h}$ values include those greater than or equal to 10, 11, 12, 13, 14, 15, 16 or 17 ng*h/mL and/or those less than or equal to 28, 27, 26, 25, 24, 23, 22, 21, 20, 19 or 18 ng*h/mL.

In one or more embodiments, administration of the oral dosage form comprising 360 mg of bupropion to a group of subjects at steady state provides an average maximum bupropion plasma concentration $C_{max}$ of 120 to 330 ng/mL, such as 150 to 260 ng/mL. Exemplary bupropion $C_{max}$ values include those greater than or equal to 120, 130, 140, 150, 160, 170, 180, 190 or 200 ng/mL and/or those less than or equal to 330, 320, 310, 300, 290, 280, 270, 260, 250, 240, 230, 220 or 210 ng/mL.

In one or more embodiments, administration of the oral dosage form comprising 360 mg of bupropion to a group of subjects at steady state provides an average bupropion plasma area under the curve $AUC_{0-24h}$ of 1,700 to 4,500 ng*h/mL, such as 2,200 to 3,600 ng*h/mL. Exemplary bupropion $AUC_{0-24h}$ values include those greater than or equal to 1,700, 1,800, 1,900, 2,000, 2,100, 2,200, 2,300, 2,400, 2,500, 2,600 or 2,700 ng*h/mL and/or those less than or equal to 4,500, 4,400, 4,300, 4,200, 4,100, 4,000, 3,900, 3,800, 3,700, 3,600, 3,500, 3,400, 3,300, 3,200, 3,100 or 3,000 ng*h/mL.

In one or more embodiments, the oral dosage form, when administered to a human subject once daily, is bioequivalent to a US FDA-approved trilayer tablet dosage form comprising naltrexone hydrochloride and bupropion hydrochloride (e.g. CONTRAVE®) administered to a human subject twice daily, under the bioequivalence parameters of: (a) a 90% Confidence Interval for AUC which is between 80% and 125%, and (b) a 90% Confidence Interval for $C_{max}$, which is between 80% and 125%.

In some embodiments, the administration of naltrexone and bupropion is continued for a period of, or of about, 1, 2, 3, 4, 6, 8, 10, 12, 16, 20, 24, 36, 48, or 52 weeks or more weeks, or a range defined by any two of the preceding values. In some embodiments, the administration of naltrexone and bupropion is continued until the reduction in symptoms of a disease, disorder, or condition is stabilized for a period of, or of about, 1, 2, 3, 4, 6, 8, 10, 12, 16, 20, 24, 36, 48, or 52 weeks or more weeks, or a range defined by any two of the preceding values. In some embodiments, administration of naltrexone and bupropion is continued until the individual no longer needs a treatment.

EXAMPLES

Example 1—Naltrexone-Containing Multilayer Extended-Release Beads

Exemplary formulations for naltrexone-containing multilayer extended-release beads are provided in Tables 1 and 2 below:

TABLE 1

| Naltrexone HCl ER Beads | | | | | | | | |
|---|---|---|---|---|---|---|---|---|
| Formulation component | Formulation N1 | | Formulation N2 | | Formulation N3 | | Formulation N4 | |
| Total wt. gain % (Based on process efficiency) | 8.6 | | 10.8 | | 13 | | 8.8 | |
| Plasticizer level (% of dry polymer) | 10 | | 10 | | 10 | | 10 | |
| Pore former level (% of dry polymer) | 25 | | 25 | | 25 | | 20 | |
| Material | mg/unit dose | % w/w (unit dose) | mg/unit dose | % w/w (unit dose) | mg/unit dose | % w/w (unit dose) | mg/unit dose | % w/w (unit dose) |
| Naltrexone Layered Beads | 118.37 | 88.85 | 118.37 | 87.12 | 118.37 | 85.45 | 115.32 | 89.95 |

TABLE 1-continued

Naltrexone HCl ER Beads

Seal Coating*

| | | | | | | | | |
|---|---|---|---|---|---|---|---|---|
| Hydroxypropyl cellulose (Klucel EXF) | 3.551 | 2.67 | 3.551 | 2.61 | 3.551 | 2.56 | 3.46 | 2.7 |
| Talc 194 M | 0.71 | 0.53 | 0.71 | 0.52 | 0.71 | 0.51 | 0.692 | 0.54 |
| Dehydrated ethanol^ | 66.756 | N/A | 66.756 | N/A | 66.756 | N/A | 65.048 | N/A |
| Total | 122.631 | 92.05 | 122.631 | 90.25 | 122.631 | 88.52 | 118.78 | 93.19 |

ER coating^^

| | | | | | | | | |
|---|---|---|---|---|---|---|---|---|
| Ethyl cellulose 20 cps | 7.848 | 5.89 | 9.81 | 7.22 | 11.773 | 8.5 | 7.246 | 5.65 |
| Hypromellose 5 cps (Methocel E5LV) | 1.962 | 1.47 | 2.453 | 1.81 | 2.943 | 2.13 | 1.449 | 1.13 |
| Triethyl citrate | 0.785 | 0.59 | 0.981 | 0.72 | 1.177 | 0.85 | 0.725 | 0.57 |
| Acetone^ | 104.537 | N/A | 130.674 | N/A | 156.811 | N/A | 92.944 | N/A |
| Dehydrated ethanol^ | 13.067 | N/A | 16.334 | N/A | 19.601 | N/A | 11.618 | N/A |
| Purified water^ | 13.067 | N/A | 16.334 | N/A | 19.601 | N/A | 11.618 | N/A |
| Total | 133.226 | 100 | 135.875 | 100 | 138.524 | 100 | 128.2 | 100 |

^Evaporates during processing,
*Solid content of Seal Coat Solution = 6.0% w/w,
^^Solid content of ER Coat Solution = 7.5% w/w, Acetone:Dehydrated ethanol:purified water = 80:10:10

TABLE 2

Naltrexone HCl ER Beads

| Formulation component | Formulation N5 |
|---|---|
| Solvent use for drug layering | 100% dehydrated ethanol |
| Drug substance to binder ratio | 90:10 |
| Antioxidant used in drug layering solution | Ascorbic acid |
| Antioxidant level | 2.9% of DS |
| BHT level | 9.4% of DS |
| Solid content of drug layering solution | 8% w/w |
| Theoretical polymer wt gain % | 7.5 |
| Theoretical total wt gain % | 10.1 |
| Plasticizer level (% of dry polymer) | 10 |
| Pore former level (% of dry polymer) | 25 |

| Material | mg/unit dose | % w/w (unit dose) |
|---|---|---|
| Substrate | | |
| MCC spheres (Actillets 350) | 60 | 46.96 |
| Seal Coating-I | | |
| Ethyl cellulose 20 cps | 7.1 | 5.56 |
| Triethyl citrate | 0.71 | 0.56 |
| Acetone^ | 77.06 | N/A |
| Dehydrated ethanol^ | 9.63 | N/A |
| Purified water^ | 9.63 | N/A |
| Total | 67.81 | 53.08 |
| Drug layering | | |
| Naltrexone HCl anhydrous (Form L) | 32 | 25.05 |
| Hydroxypropyl cellulose (Klucel EXF) | 3.2 | 2.5 |
| Ascorbic acid | 0.92 | 0.72 |
| Butylated hydroxy toluene (BHT) | 3 | 2.35 |
| Dehydrated ethanol^ | 449.88 | N/A |
| Total | 106.93 | 83.7 |

TABLE 2-continued

Naltrexone HCl ER Beads

| | | |
|---|---|---|
| Seal Coating-II | | |
| Hydroxypropyl cellulose (Klucel EXF) | 3.21 | 2.51 |
| Dehydrated ethanol^ | 36.89 | N/A |
| Total | 110.138 | 86.21 |
| ER coating | | |
| Ethyl cellulose 20 cps | 10.297 | 8.06 |
| Hypromellose 5 cps (Methocel E5LV) | 2.574 | 2.02 |
| Triethyl citrate | 1.03 | 0.81 |
| Acetone^ | 131.157 | N/A |
| Dehydrated ethanol^ | 17.145 | N/A |
| Purified water^ | 17.145 | N/A |
| Total | 124.039 | 97.1 |
| Film (Top) coating | | |
| Opadry TF white 266F180001 | 3.721 | 2.91 |
| Dehydrated ethanol^ | 70.699 | N/A |
| Total | 127.76 | 100 |

Figure 2:
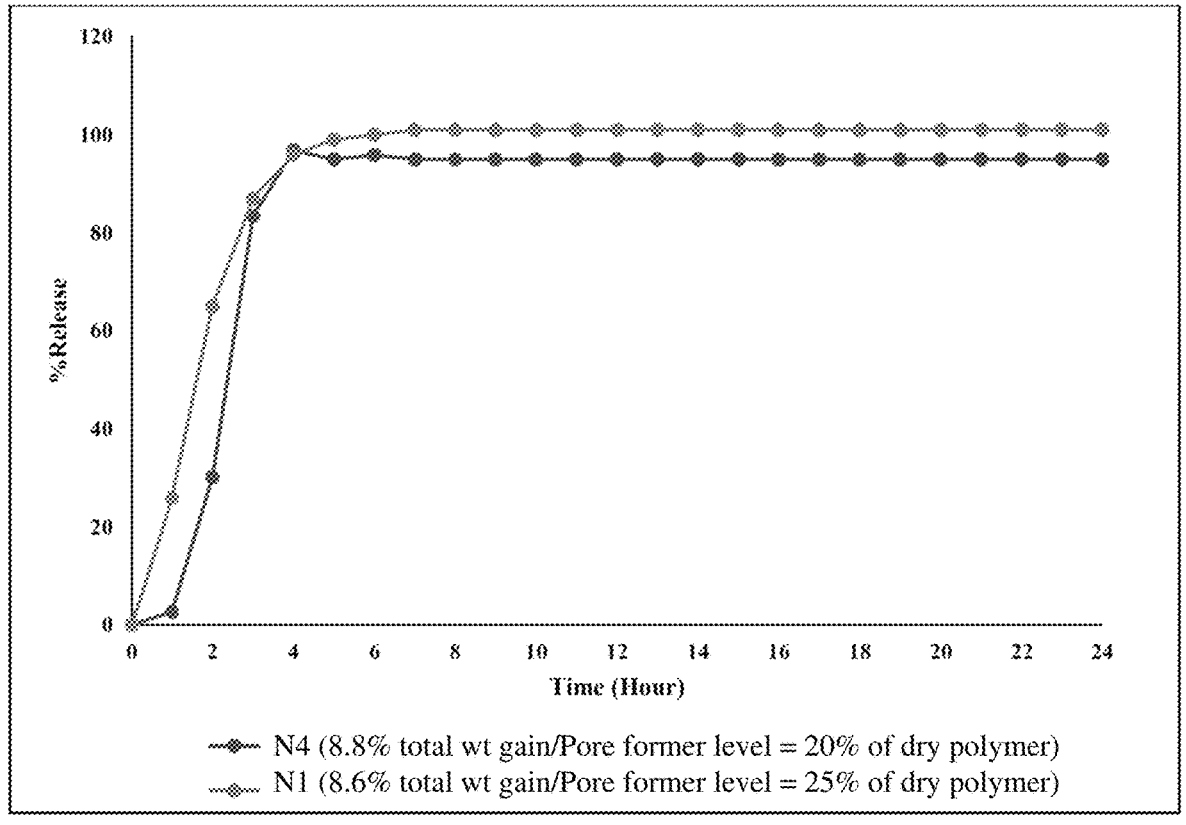
FIG. 2 shows the in vitro dissolution profiles of various naltrexone extended-release formulations.

^Evaporates during processing, Solid content of Seal Coat-I Solution = 7.5% w/w, Acetone:Dehydrated ethanol:purified water = 80:10:10, ¥Solid content of Drug layering dispersion = 8.0% w/w, Solid content of Seal Coat-II Solution = 6.0% w/w, Solid content of ER Coat Solution = 7.5% w/w, Acetone:Dehydrated ethanol:purified water = 80:10:10, Solid content of Film coat dispersion = 8.0% w/w, The in vitro dissolution naltrexone-containing multilayer beads of Formulations N1, N2, N3 and N4 were tested in USP Apparatus 1 Basket Method at 100 rpm in a dissolution medium of 900 mL purified water at 37° C. The in vitro release of naltrexone for Formulations N1, N2 and N3 is shown in FIG. 1 and Formulations N1 and N4 is shown in FIG. 2. As can be seen from FIG. 1, the release rate of the naltrexone HCl is inversely proportional to the coating thickness or polymer weight gain. As can be seen from FIG. 2, the release rate of the naltrexone HCl is increased by higher levels of pore former (20% pore former for N4 and 25% pore former for N1).

Figure 3:
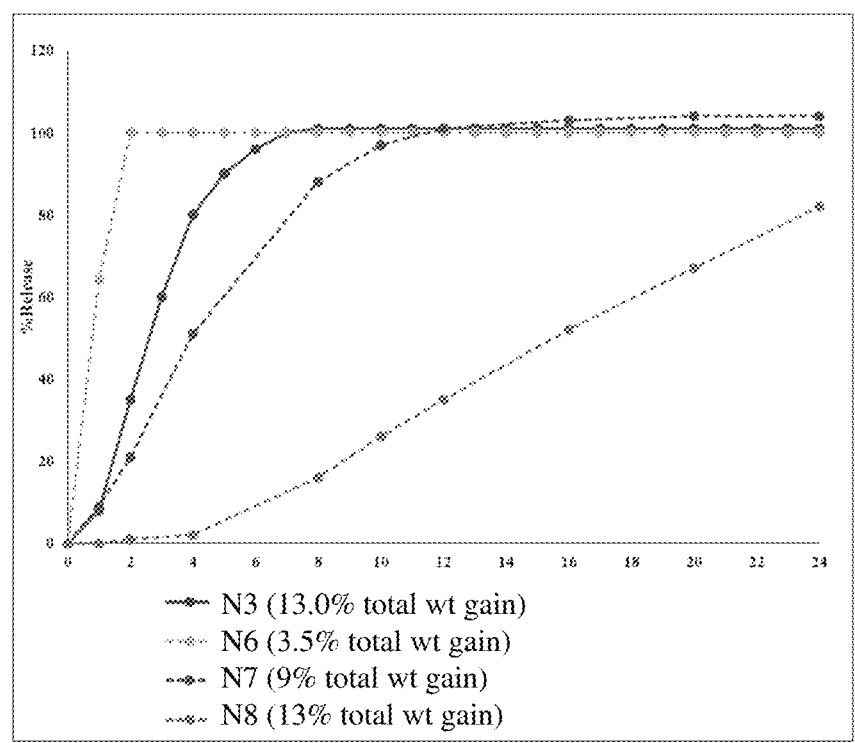
FIG. 3 shows the in vitro dissolution profiles of various naltrexone extended-release formulations.

The in vitro dissolution naltrexone-containing multilayer beads of Formulation N5 with various levels of ER coating (N6=3.5% total wt gain, N7=9% total weight gain and N8=13% total weight gain) were tested in USP Apparatus 1 Basket Method at 100 rpm in a dissolution medium of 900 mL purified water at 37° C. The in vitro release of naltrexone for Formulations N6, N7 and N8 compared to N3 is shown in FIG. 3. Although N3 and N8 have similar weight gain, N8 has a slower release rate due to the increased homogeneity/sphericity of the naltrexone beads. Accordingly, the release rate for beads with a high level of homogeneity/sphericity can be increased by lowering the ER coating thickness/weight gain, increasing plasticizer levels and/or increasing pore former levels.

Based on in vitro release profiles, pharmacokinetic simulations for rate and extent of absorption at steady state ($C_{max_{(ss)}}$ and $AUC_{ss}$) were generated for selected prototypes of naltrexone HCl ER beads and compared with 16 mg BID (twice a day) dosing of CONTRAVE® tablets. The results are shown in FIG. 4 and Table 3 below:

TABLE 3

| Pharmacokinetic (PK) parameters of prototypes of Naltrexone HCl ER beads for 32 mg QD & CONTRAVE ® tablets 16 mg BID. | | | | | | | |
|---|---|---|---|---|---|---|---|
| Type | Dose of Naltrexone HCl (mg) | Dosing frequency | Total daily dose of Naltrexone HCl (mg) | $C_{maxss}$ (ng/ml) | $C_{minss}$ (ng/ml) | AUCss (ng * h/ml) | Fa (%) |
| CONTRAVE ® tablets | 2 * 8 | BID | 32 | 1.44 | 0.29 | 17.4 | 83 |
| N1 | 1 * 32 | QD | 32 | 2.16 | 0.13 | 16.7 | 80 |
| N2 | 1 * 32 | QD | 32 | 1.67 | 0.15 | 15.8 | 76 |
| N3 | 1 * 32 | QD | 32 | 1.45 | 0.16 | 15.4 | 74 |

Figure 4:
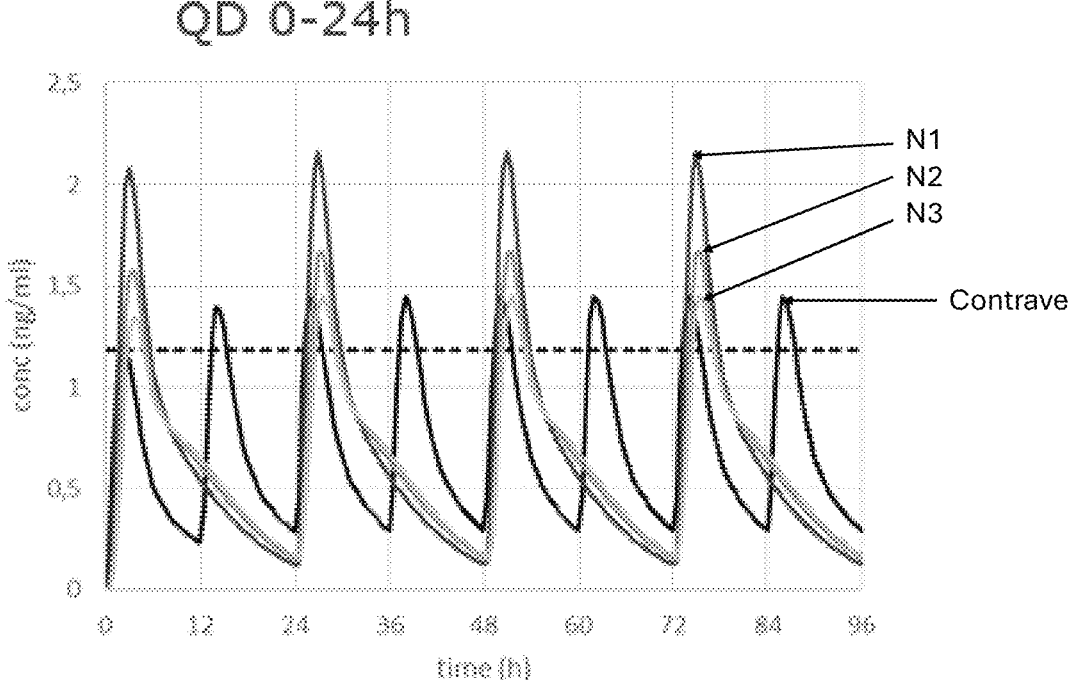
FIG. 4 shows pharmacokinetic simulations of various naltrexone extended-release formulations.

*Simulations are generated using Gastroplus (G+) software, which removes all existing formulation in the GI tract when a new dose is given Based on pharmacokinetic parameters shown in FIG. 4 and Table 3, formulations N2 and N3 are simulated to fall within bioequivalence criteria of 80%-120% for $C_{max_{(ss)}}$ and $AUC_{ss}$ when comparing 32 mg QD (once a day) dosing of formulations N2 and N3 with 16 mg BID (twice a day) dosing of CONTRAVE® tablets.

Example 2—Bupropion-Containing Multilayer Extended-Release Beads

Exemplary formulations for bupropion-containing multilayer extended-release beads are provided in Tables 4, 5 and 6 below:

TABLE 4

| Bupropion HCl ER Beads | | | | | | | | |
|---|---|---|---|---|---|---|---|---|
| Formulation component | Formulation B1 | | Formulation B2 | | Formulation B3 | | Formulation B4 | |
| Drug loading in core beads (% w/w) | 79.6 | | 79.6 | | 79.6 | | 79.6 | |
| Practical polymer wt. gain (%) (Based on process efficiency) | 4.3 | | 5.1 | | 6 | | 7.7 | |
| Total wt. gain % (Based on process efficiency) | 6.8 | | 8.1 | | 9.5 | | 12.2 | |
| Plasticizer level (% of dry polymer) | 21.3 | | 21.3 | | 21.3 | | 21.3 | |
| Pore former level (% of dry polymer) | 25 | | 25 | | 25 | | 25 | |
| Solvent System | Aqueous | | Aqueous | | Aqueous | | Aqueous | |
| Material | mg/ unit dose | % w/w (unit dose) | mg/ unit dose | % w/w (unit dose) | mg/ unit dose | % w/w (unit dose) | mg/ unit dose | % w/w (unit dose) |
| Bupropion Core Beads | 452.25 | 90.89 | 452.25 | 89.82 | 452.25 | 88.66 | 452.25 | 86.53 |
| Seal Coating* | | | | | | | | |
| Hypromellose 5 cps (Methocel E5LV) | 13.568 | 2.73 | 13.568 | 2.69 | 13.568 | 2.66 | 13.568 | 2.6 |

TABLE 4-continued

Bupropion HCl ER Beads

| Formulation component | Formulation B1 | | Formulation B2 | | Formulation B3 | | Formulation B4 | |
|---|---|---|---|---|---|---|---|---|
| L-Cysteine hydrochloride monohydrate | 0.136 | 0.03 | 0.136 | 0.03 | 0.136 | 0.03 | 0.136 | 0.03 |
| Purified water^ | 214.696 | N/A | 214.696 | N/A | 214.696 | N/A | 214.696 | N/A |
| Total | 465.954 | 93.65 | 465.954 | 92.54 | 465.954 | 91.35 | 465.954 | 89.16 |
| | | | ER coating^^^ | | | | | |
| Surelease ® E-7 19020 EC Clear dispersion Type-Bα | 26.634 | 5.35 | 31.601 | 6.28 | 37.177 | 7.29 | 47.711 | 9.13 |
| Hypromellose 5 cps (Methocel E5LV) | 5.009 | 1.01 | 5.941 | 1.18 | 6.989 | 1.37 | 8.97 | 1.72 |
| Purified water^ | 20.099 | N/A | 23.845 | N/A | 28.053 | N/A | 36.002 | N/A |
| Total | 497.597 | 100 | 503.496 | 100 | 510.12 | 100 | 522.635 | 100 |

^Evaporates during processing,
*Solid content of Seal Coat Solution= 6.0% w/w,
^^^Solid content of ER Coat dispersion = 15% w/w,
**Surelease E-7 19020 dispersion contains 25% Solid content (18.8% of Ethyl cellulose 20 cps, 4% of Dibutyl sebacate, 2.2% of Oleic acid) and 75% liquid content (70.6% of purified water & 4.4% of Ammonium hydroxide 28%).

TABLE 5

Bupropion HCl ER Beads

| Formulation component | Formulation B5 | Formulation B6 | Formulation B7 |
|---|---|---|---|
| Drug loading in core beads (% w/w) | 70 | 70 | 70 |
| Practical polymer wt. gain (%) (Based on process efficiency) | 6 | 9.5 | 13 |
| Total wt. gain % (Based on process efficiency) | 8.1 | 12.8 | 17.6 |
| Plasticizer level (% of dry polymer) | 10 | 10 | 10 |
| Pore former level (% of dry polymer) | 25 | 25 | 25 |
| Solvent System | Organic | Organic | Organic |

| Material | mg/unit dose | % w/w (unit dose) | mg/unit dose | % w/w (unit dose) | mg/unit dose | % w/w (unit dose) |
|---|---|---|---|---|---|---|
| Bupropion Core Beads | 514.32 | 89.79 | 514.32 | 86.03 | 514.32 | 82.57 |
| | | Seal Coating* | | | | |
| Hypromellose 5 cps (Methocel E5LV) | 15.43 | 2.69 | 15.43 | 2.58 | 15.43 | 2.48 |
| L-Cysteine hydrochloride monohydrate | 0.154 | 0.03 | 0.154 | 0.03 | 0.154 | 0.03 |
| Purified water^ | 244.149 | N/A | 244.149 | N/A | 244.149 | N/A |
| Total | 529.904 | 92.51 | 529.904 | 88.64 | 529.904 | 85.08 |
| | | ER coating^^^ | | | | |
| Ethyl cellulose 20 cps | 31.794 | 5.55 | 50.34 | 8.42 | 68.888 | 11.06 |
| Hypromellose 5 cps (Methocel E5LV) | 7.949 | 1.39 | 12.585 | 2.11 | 17.222 | 2.77 |
| Dibutyl sebacate | 3.18 | 0.56 | 5.034 | 0.84 | 6.889 | 1.11 |
| Acetone^ | 423.507 | N/A | 670.529 | N/A | 920.07 | N/A |
| Dehydrated ethanol^ | 52.938 | N/A | 83.816 | N/A | 115.09 | N/A |
| Purified water^ | 52.938 | N/A | 83.816 | N/A | 115.09 | N/A |
| Total | 497.597 | 100 | 597.863 | 100 | 622.903 | 100 |

^Evaporates during processing,
*Solid content of Seal Coat Solution = 6.0% w/w,
^^^Solid content of ER Coat dispersion = 7.5%, Acetone:Dehydrated ethanol:purified water = 80:10:10.

TABLE 6

| | Bupropion HCl ER Beads | | |
|---|---|---|---|
| Formulation component | Formulation B8 | Formulation B9 | Formulation B10 |
| Drug loading in core beads (% w/w) | 75 | 75 | 70 |
| Practical polymer wt. gain (%) (Based on process efficiency) | 7 | 13 | 4.8 |
| Total wt. gain % (Based on process efficiency) | 11.1 | 20.5 | 6 |
| Plasticizer level (% of dry polymer) | 21.3 | 21.3 | 10 |
| Pore former level (% of dry polymer) | 25 | 25 | 15 |
| Solvent System | Aqueous | Aqueous | Organic |

| Material | mg/unit dose | % w/w (unit dose) | mg/unit dose | % w/w (unit dose) | mg/unit dose | % w/w (unit dose) |
|---|---|---|---|---|---|---|
| Bupropion Core Beads | 480 | 86.94 | 480 | 80.52 | 514.32 | 91.57 |
| Seal Coating* | | | | | | |
| Hypromellose 5 cps (Methocel E5LV) | 14.4 | 2.61 | 14.4 | 2.42 | 15.43 | 2.75 |
| L-Cysteine hydrochloride monohydrate | 0.144 | 0.03 | 0.144 | 0.02 | 0.154 | 0.03 |
| Purified water^ | 227.856 | N/A | 227.856 | N/A | 244.149 | N/A |
| Total | 494.544 | 89.58 | 494.544 | 82.96 | 529.04 | 94.35 |
| ER coating^^^ | | | | | | |
| Surelease ® E-7 19020 EC Clear dispersion Type-Bα | 46.035 | 8.34 | 85.493 | 14.34 | N/A | N/A |
| Ethyl cellulose 20 cps | N/A | N/A | N/A | N/A | 25.435 | 4.53 |
| Hypromellose 5 cps (Methocel E5LV) | 11.509 | 2.08 | 16.073 | 2.7 | 3.815 | 0.68 |
| Dibutyl sebacate | N/A | N/A | N/A | N/A | 2.544 | 0.45 |
| Acetone^ | N/A | N/A | N/A | N/A | 351.345 | N/A |
| Dehydrated ethanol^ | N/A | N/A | N/A | N/A | 43.918 | N/A |
| Purified water^ | 122.47 | N/A | 226.202 | N/A | 43.918 | N/A |
| Total | 552.088 | 100 | 596.11 | 100 | 561.698 | 100 |

^Evaporates during processing,

*Solid content of Seal Coat Solution = 6.0% w/w,

^^^Solid content of ER Coat dispersion = 15% w/w for B8 and B9 and 7.5% w/w for B10,

**Surelease E-7 19020 dispersion contains 25% Solid content (18.8% of Ethyl cellulose 20 cps, 4% of Dibutyl sebacate, 2.2% of Oleic acid) and 75% liquid content (70.6% of purified water & 4.4% of Ammonium hydroxide 28%), Acetone:Dehydrated ethanol:purified water for B10 = 80:10:10.

TABLE 7

| | Bupropion HCl ER Beads | |
|---|---|---|
| Formulation component | Formulation B11 | |
| Drug loading in core beads (% w/w) | 82 | |
| Theoretical polymer wt gain % | 6 | |
| Theoretical total wt gain % | 8.1 | |
| Plasticizer level (% of dry polymer) | 10 | |
| Pore former level (% of dry polymer) | 25 | |
| Material | mg/unit dose | % w/w (unit dose) |
| Core beads | | |
| Bupropion hydrochloride (Micronized) | 360 | 72.47 |
| Microcrystalline cellulose (Avicel PH 101) | 59.95 | 12.07 |
| Methylcellulose (Methocel A15LV) | 12.49 | 2.51 |
| L-Cysteine hydrochloride monohydrate | 4.39 | 0.88 |
| Colloidal anhydrous silica (Aerosil ® 200) | 2.2 | 0.44 |
| Purified water^ | q.s. | q.s. |
| Total | 439.03 | 88.37 |
| Seal Coating | | |
| Hypromellose 5 cps (Methocel E5LV) | 13.568 | 2.73 |
| L-Cysteine hydrochloride monohydrate | 0.136 | 0.03 |
| Purified water^ | 214.696 | N/A |
| Total | 452.734 | 91.13 |
| ER coating | | |
| Ethyl cellulose 20 cps | 27.164 | 5.47 |
| Hypromellose 5 cps (Methocel E5LV) | 6.791 | 1.37 |
| Dibutyl sebacate | 2.716 | 0.55 |

TABLE 7-continued

| Bupropion HCl ER Beads | | |
|---|---|---|
| Acetone^ | 361.82 | N/A |
| Dehydrated ethanol^ | 45.23 | N/A |
| Purified water^ | 45.23 | N/A |
| Total | 489.405 | 98.52 |
| Film (Top) coating | | |
| Opadry TF 271ZA100000 purple | 7.341 | 1.48 |
| Dehydrated ethanol^ | 66.069 | N/A |
| Total | 496.746 | 100 |

Figure 5:
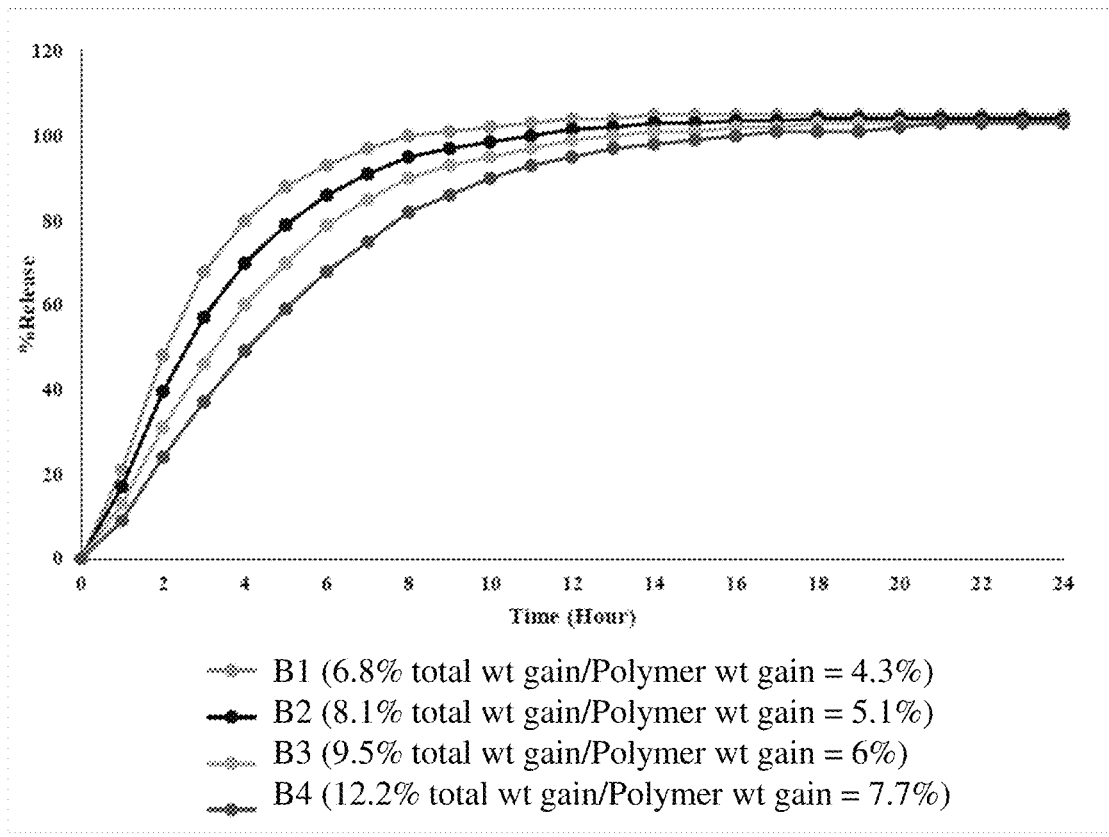
FIG. 5 shows the in vitro dissolution profiles of various bupropion extended-release formulations.
Figure 6:
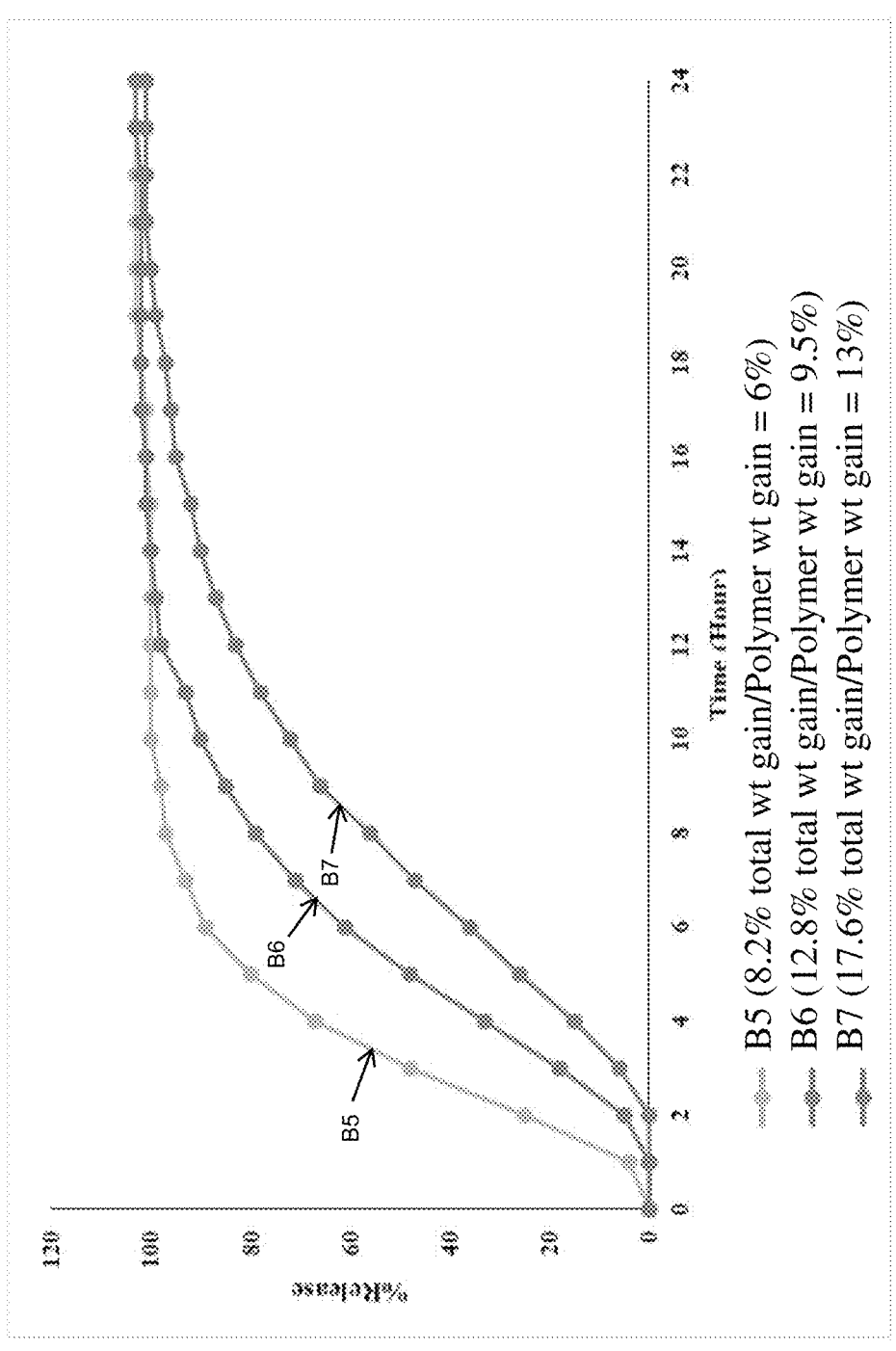
FIG. 6 shows the in vitro dissolution profiles of various bupropion extended-release formulations.
Figure 7:
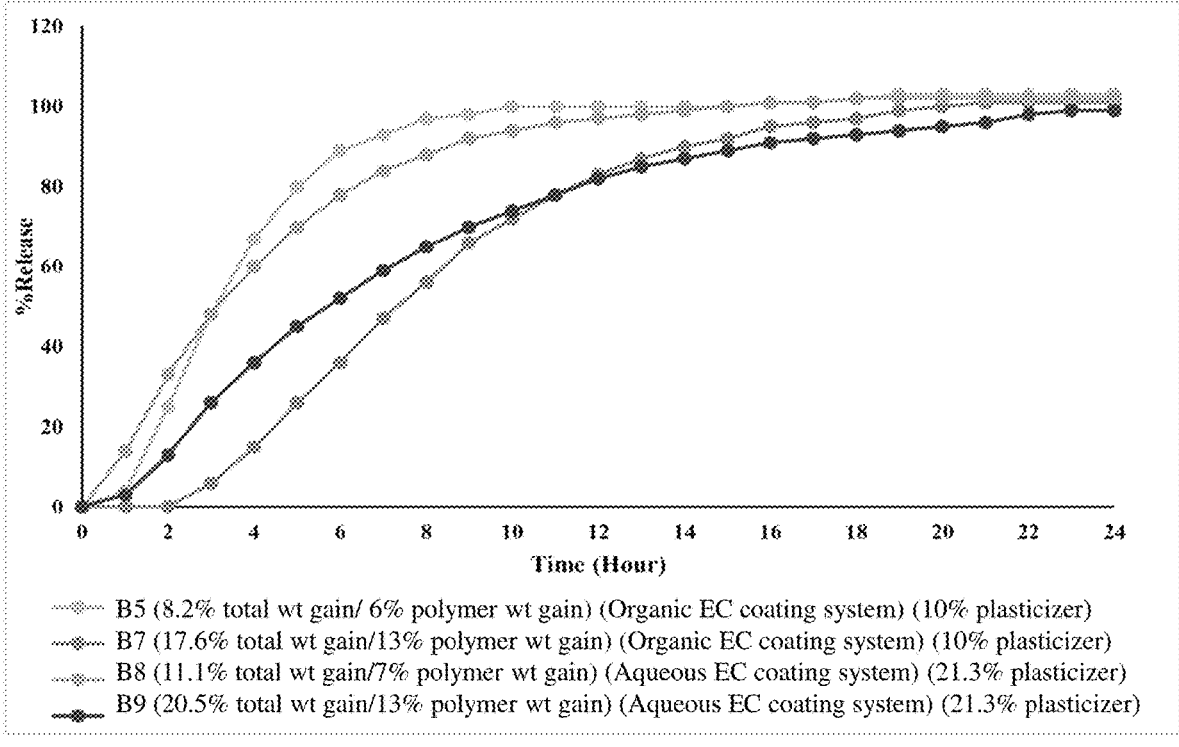
FIG. 7 shows the in vitro dissolution profiles of various bupropion extended-release formulations.
Figure 8:
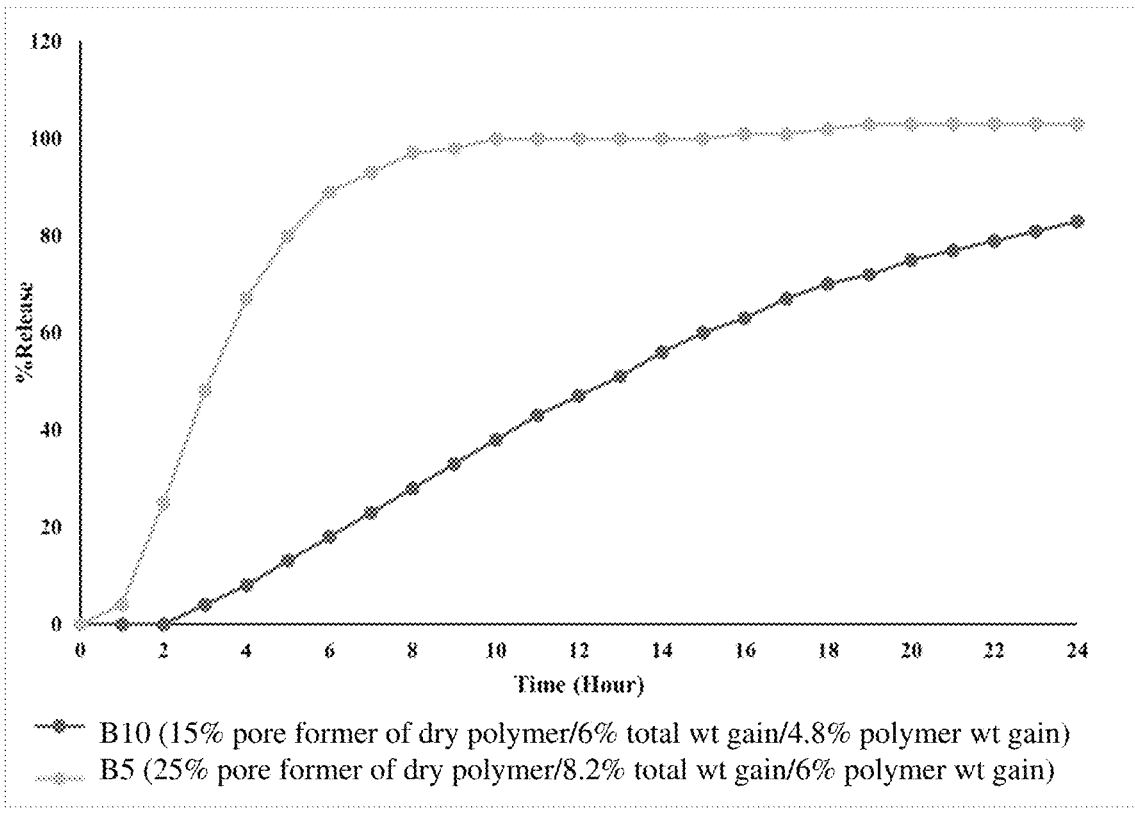
FIG. 8 shows the in vitro dissolution profiles of various bupropion extended-release formulations.

^Evaporates during processing, Solid content of Seal Coat Solution = 6.0% w/w, ^^ Solid content of ER Coat dispersion = 7.5% w/w, Solid content of Film Coat dispersion = 10% w/w The in vitro dissolution of the bupropion-containing multilayer beads of Formulations B1, B2, B3, B4, B5, B6, B7, B8, B9 and B10 were tested in USP Apparatus 1 Basket Method at 100 rpm in a dissolution medium of 900 mL purified water at 37° C. The in vitro release of bupropion of Formulations B1, B2, B3 and B4 is shown in FIG. 5. As can be seen from FIG. 5, the release rate of the bupropion HCl is inversely proportional to the coating thickness or polymer weight gain. The in vitro release of bupropion Formulations B5, B6 and B7 is shown in FIG. 6. Again, as can be seen from FIG. 6, the release rate of the bupropion HCl is inversely proportional to the coating thickness or polymer weight gain. The in vitro release of bupropion Formulations B5, B7, B8 and B9 is shown in FIG. 7. As can be seen from FIG. 7, the release rate of the bupropion HCl is increased by higher levels of plasticizer (21.1% vs 10%). The in vitro release of bupropion Formulations B5 and B10 is shown in FIG. 8. As can be seen from FIG. 8, the release rate of the bupropion HCl is increased by higher levels of pore former (25% pore former for B5 and 15% pore former for B10).

Figure 9:
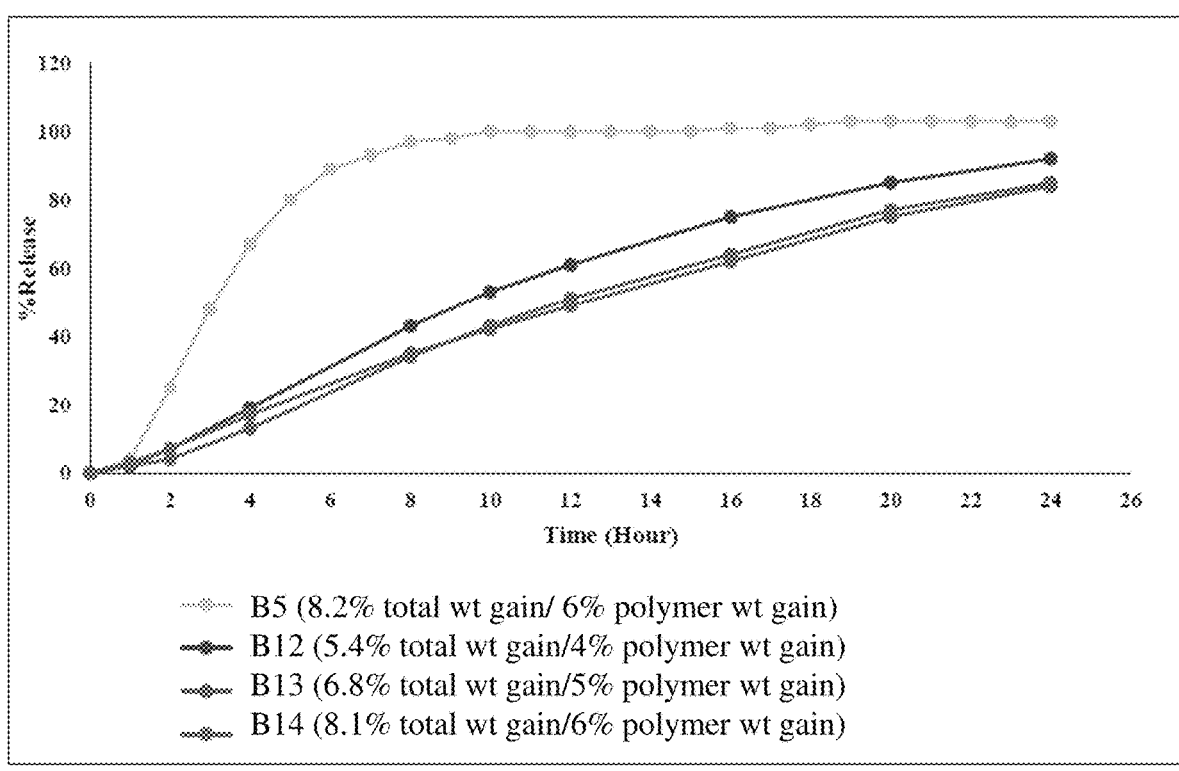
FIG. 9 shows the in vitro dissolution profiles of various bupropion extended-release formulations.

The in vitro dissolution bupropion-containing multilayer beads of Formulation B11 with various levels of ER coating (B12=5.4% total wt gain, B13=6.8% total weight gain and B14=8.1% total weight gain) were tested in USP Apparatus 1 Basket Method at 100 rpm in a dissolution medium of 900 mL purified water at 37° C. The in vitro release of bupropion for Formulations B12, B13 and B14 compared to B5 shown in FIG. 9. Although B5 and B14 have similar weight gain, B14 has a slower release rate due to the increased homogeneity/sphericity of the bupropion beads. Accordingly, the release rate for beads with a high level of homogeneity/sphericity can be increased by lowering the ER coating thickness/weight gain, increasing plasticizer levels and/or increasing pore former levels.

Based on in vitro release profiles, pharmacokinetic simulations for rate and extent of absorption at steady state ($C_{max_{(ss)}}$ and $AUC_{ss}$) were generated for selected prototypes of bupropion HCl ER beads and compared with 360 mg BID (twice a day) dosing of CONTRAVE® tablets. The results are shown in Table 8 below:

TABLE 8

Pharmacokinetic (PK) parameters of prototypes of Bupropion HCl ER beads for 360 mg QD & CONTRAVE ® tablets 32 mg BID.

| Type | Dose of Bupropion HCl (mg) | Dosing frequency | Total daily dose of Bupropion HCl (mg) | $C_{maxss}$ (ng/ml) | $C_{minss}$ (ng/ml) | AUCss (ng * h/ml) | Fa (%) |
|---|---|---|---|---|---|---|---|
| Contrave ® tablets | 2 * 90 | BID | 360 | 200 | 71 | 2852 | 96 |
| B1 | 1 * 360 | QD | 360 | 258 | 42 | 2777 | 93 |
| B2 | 1 * 360 | QD | 360 | 220 | 44 | 2714 | 91 |
| B3 | 1 * 360 | QD | 360 | 187 | 46 | 2641 | 89 |
| B5 | 1 * 360 | QD | 360 | 202 | 45 | 2693 | 90 |
| B6 | 1 * 360 | QD | 360 | 152 | 47 | 2467 | 83 |
| B7 | 1 * 360 | QD | 360 | 135 | 47 | 2219 | 74 |

Figure 10:
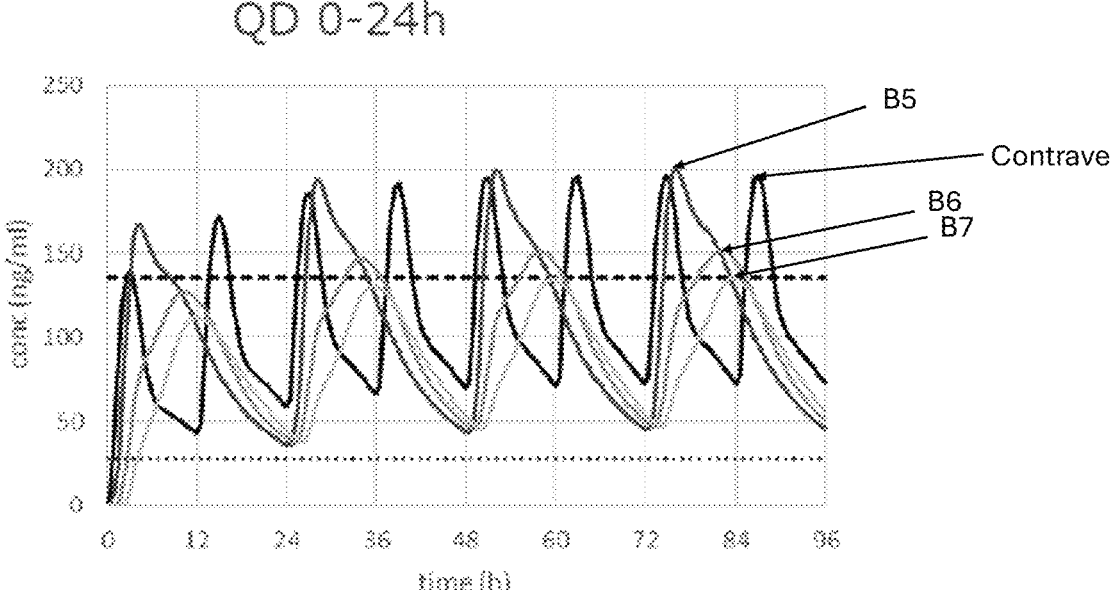
FIG. 10 shows pharmacokinetic simulations of various bupropion extended-release formulations.

*Simulations are generated using Gastroplus (G+) software, which removes all existing formulation in the GI tract when a new dose is given Based on pharmacokinetic parameters shown in FIG. 10 and Table 8, formulations B2, B3 and B5 are simulated to fall within bioequivalence criteria of 80%-120% for $C_{max_{(ss)}}$ and $AUC_{ss}$ when comparing 360 mg QD (once a day) dosing of formulations B2, B3 and B5 16 mg BID (twice a day) dosing of CONTRAVE® tablets.

Reference throughout this specification to "one embodiment," "certain embodiments," "various embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in various embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein provided a description with reference to particular embodiments, it is to be understood that these embodiments are merely illustrative of the principles and applications of the disclosure. It will be apparent to those skilled in the art that various modifications and variations can be made to the present disclosure without departing from the spirit and scope thereof. Thus, it is intended that the present disclosure include modifications and variations that are within the scope of the appended claims and their equivalents.

What is claimed is:

1. An oral dosage form comprising a plurality of naltrexone-containing beads and a plurality of bupropion-containing beads, wherein the naltrexone-containing beads are extended-release, multilayer beads comprising:

a core particle, wherein the core particle is drug-free;

an optional seal coating coated on the surface of the core particle;

a drug layer comprising naltrexone, or a salt thereof, coated on the surface of the core particle or, when present, the seal coating;

a non-aqueous barrier coating coated on the surface of the drug layer;

an extended-release coating coated on the surface of the barrier coating; and an optional top coating coated on the surface of the extended-release coating;

wherein the naltrexone-containing beads have an in vitro naltrexone dissolution profile in a dissolution test of USP Apparatus 1 Basket Method at 100 rpm in a dissolution medium of water at 37° C. of:

i. 2% to 20% of the naltrexone released in one hour;

ii. 10% to 50% of the naltrexone released in two hours; and iii. 50% to 90% of the naltrexone released in four hours; and wherein the bupropion-containing beads are extended-release, multilayer beads comprising:

a core particle comprising bupropion, or a salt thereof;

an optional seal coating coated on the surface of the core particle;

an extended-release coating coated on the surface of the core particle, or if present, on the surface of the seal coating; and an optional top coating coated on the surface of the extended-release coating.

2. The oral dosage form of claim 1, wherein the core particle of the naltrexone-containing beads is selected from a microcrystalline cellulose particle, a silica particle, and a sugar particle.

3. The oral dosage form of claim 1, wherein the drug layer of the naltrexone-containing beads comprises about 50% to about 95% by weight of naltrexone, or a salt thereof.

4. The oral dosage form of claim 3, wherein the drug layer of the naltrexone-containing beads comprises further comprises a low viscosity binder selected from Hypromellose 3 cps, Hypromellose 5 cps, and Hydroxypropyl cellulose.

5. The oral dosage form of claim 3, wherein the naltrexone comprises an anhydrous polymorph of the hydrochloride salt (Form L) and/or an ethanol solvate of the hydrochloride salt (Form F).

6. The oral dosage form of claim 5, wherein the non-aqueous barrier coating of the naltrexone-containing beads is prepared under anhydrous conditions.

7. The oral dosage form of claim 6, wherein the non-aqueous barrier coating of the naltrexone-containing beads is prepared using a solvent selected from the group consisting of class 3 solvents.

8. The oral dosage form of claim 1, wherein the naltrexone-containing beads comprise no more than 0.5% 2-chloro-10α-hydroxynaltrexone, based on the weight of naltrexone.

9. The oral dosage form of claim 1, wherein the bupropion, or a salt thereof, is present in the core particle of bupropion-containing beads ≥70% w/w.

10. The oral dosage form of claim 1, wherein the bupropion-containing beads comprise no more than 1% (2R,3R, 5R)-2-(3-chlorophenyl)-2-hydroxy-3-methylthiomorpholine-5-carboxylic acid (RRR-CHMTCA) and no more than 0.5% (2S,3S,5R)-2-(3-chlorophenyl)-2-hydroxy-3-methylthiomorpholine-5-carboxylic acid (SSR-CHMTCA), based on the weight of bupropion.

11. The oral dosage form of claim 1, wherein the extended-release coating of the naltrexone-containing beads and/or the bupropion-containing beads comprises a release controlling polymer and a pore former.

12. The oral dosage form of claim 11, wherein the release controlling polymer is present in an amount of about 5% to about 25% by weight of the naltrexone-containing beads and/or the bupropion-containing beads.

13. The oral dosage form of claim 12, wherein the extended-release coating of the naltrexone-containing beads and/or the bupropion-containing beads comprises a plasticizer present in an amount of about 5% to about 15% of dry polymer concentration.

14. The oral dosage form of claim 1, wherein the naltrexone-containing beads comprise about 8 to about 32 mg of naltrexone or a salt thereof; and wherein the bupropion-containing beads comprise about 90 mg to about 360 mg of bupropion or a salt thereof.

15. The oral dosage form of claim 14, wherein the in vitro naltrexone dissolution profile in the dissolution test is 30% to 80% of the naltrexone released in three hours.

16. The oral dosage form of claim 15, wherein the bupropion-containing beads have an in vitro bupropion dissolution profile in a dissolution test of USP Apparatus 1 Basket Method at 100 rpm in a dissolution medium of water at 37° C. of:

i. less than 30% of the bupropion released in one hour; or ii. less than 60% of the bupropion released in two hours.

17. The oral dosage form of claim 16, wherein the in vitro bupropion dissolution profile in the dissolution test is:

i. 2% to 20% of the bupropion released in one hour; and ii. 10% to 50% of the bupropion released in two hours.

18. The oral dosage form of claim 14, wherein the in vitro naltrexone dissolution profile in the dissolution test is 30% to 80% of the naltrexone released in three hours;

wherein the bupropion-containing beads have an in vitro bupropion dissolution profile in a dissolution test of USP Apparatus 1 Basket Method at 100 rpm in a dissolution medium of water at 37° C. of:

i. 2% to 20% of the bupropion released in one hour;

ii. 10% to 50% of the bupropion released in two hours; and iii. 50% to 90% of the bupropion released in four hours.

19. The oral dosage form of claim 14, wherein administration of the oral dosage form to a group of subjects at steady state provides an average maximum naltrexone plasma concentration $C_{max}$ of 1.1 to 1.8 ng/mL.

20. The oral dosage form of claim 14, wherein administration of the oral dosage form to a group of subjects at steady state provides an average naltrexone plasma area under the curve $AUC_{0-24h}$ of 13 to 22 ng*h/mL.

21. The oral dosage form of claim 14, wherein administration of the oral dosage form to a group of subjects at steady state provides an average maximum bupropion plasma concentration $C_{max}$ of 150 to 260 ng/mL.

22. The oral dosage form of claim 14, wherein administration of the oral dosage form to a group of subjects at steady state provides an average bupropion plasma area under the curve $AUC_{0-24h}$ of 2,200 to 3,600 ng*h/mL.

23. The oral dosage form of claim 14, wherein the oral dosage form, when administered to a human subject once daily, is bioequivalent to a US FDA-approved trilayer tablet dosage form comprising naltrexone hydrochloride and bupropion hydrochloride administered to a human subject twice daily, under the bioequivalence parameters of: (a) a 90% Confidence Interval for AUC which is between 80% and 125%, and (b) a 90% Confidence Interval for Cmax, which is between 80% and 125%.

24. The oral dosage form of claim 1, wherein the naltrexone salt is naltrexone hydrochloride.

25. The oral dosage form of claim 24, wherein the naltrexone hydrochloride is substantially free of amorphous naltrexone hydrochloride.

26. The oral dosage form of claim 1, wherein the oral dosage form comprises a capsule containing the plurality of naltrexone-containing beads and the plurality of bupropion-containing beads.

27. A method of treating overweight or obesity in a subject in need thereof, the method comprising administering to the subject the oral dosage form of claim 1.

28. A method of treating overweight or obesity in a subject in need thereof, the method comprising:

administering to the subject a first oral dosage form comprising about 8 mg of naltrexone or salt thereof and about 90 mg of bupropion or salt thereof, wherein the first oral dosage form is administered once a day for a first week;

administering to the subject a second oral dosage form comprising about 16 mg of naltrexone or salt thereof and about 180 mg of bupropion or salt thereof, wherein the second oral dosage form is administered once a day for a second week;

administering to the subject a third oral dosage form comprising about 24 mg of naltrexone or salt thereof and about 270 mg of bupropion or salt thereof, wherein the third oral dosage form is administered once a day for a third week; and administering to the subject a fourth oral dosage form comprising about 32 mg of naltrexone or salt thereof and about 360 mg of bupropion or salt thereof, wherein the fourth oral dosage form is administered once a day for a fourth and subsequent weeks, wherein each of the first oral dosage form, the second oral dosage form, the third oral dosage form and the fourth oral dosage form comprises a plurality of naltrexone-containing beads and a plurality of bupropion-containing beads, wherein the naltrexone-containing beads are extended-release, multilayer beads and wherein the bupropion-containing beads are extended-release, multilayer beads;

wherein the naltrexone-containing beads have an in vitro naltrexone dissolution profile in a dissolution test of USP Apparatus 1 Basket Method at 100 rpm in a dissolution medium of water at 37° C. of:

i. 2% to 20% of the naltrexone released in one hour;

ii. 10% to 50% of the naltrexone released in two hours; and iii. 50% to 90% of the naltrexone released in four hours.

29. A method of treating overweight or obesity in a subject in need thereof, the method comprising administering to the subject an oral dosage form comprising naltrexone and bupropion once a day, wherein the oral dosage form comprises a naltrexone extended-release formulation having an in vitro naltrexone dissolution profile in a dissolution test of USP Apparatus 1 Basket Method at 100 rpm in a dissolution medium of water at 37° C. of:

iv. 2% to 20% of the naltrexone released in one hour;

v. 10% to 50% of the naltrexone released in two hours; and vi. 50% to 90% of the naltrexone released in four hours.

30. The method of claim 29, wherein the oral dosage form is a capsule.

* * * * *